US012618833B2

(12) United States Patent
Wolfrum et al.

(10) Patent No.: US 12,618,833 B2
(45) Date of Patent: May 5, 2026

(54) SENSING OF MOLECULES BY ELECTROCHEMICAL DETECTION OF NANOPARTICLES

(71) Applicant: TECHNISCHE UNIVERSITÄT MÜNCHEN, Munich (DE)

(72) Inventors: Bernhard Wolfrum, Unterschleissheim (DE); Nouran Yehia Adly Hassan, Munich (DE); Philipp Rinklin, Unterschleissheim (DE); Leroy Grob, Munich (DE); Oliver Hayden, Moosburg an der Isar (DE); Lennart Weiss, Munich (DE); Phu Duy Tran, Salisbury (AU); Benjamin Thierry, Munich (DE)

(73) Assignee: TECHNISCHE UNIVERSITÄT MÜNCHEN, Munich (DE)

( * ) Notice: Subject to any disclaimer, the term of this patent is extended or adjusted under 35 U.S.C. 154(b) by 945 days.

(21) Appl. No.: 17/792,185

(22) PCT Filed: Jan. 15, 2021

(86) PCT No.: PCT/EP2021/050793
§ 371 (c)(1),
(2) Date: Jul. 12, 2022

(87) PCT Pub. No.: WO2021/144413
PCT Pub. Date: Jul. 22, 2021

(65) Prior Publication Data
US 2023/0041136 A1    Feb. 9, 2023

(30) Foreign Application Priority Data
Jan. 17, 2020    (EP) .................................... 20152532

(51) Int. Cl.
*G01N 33/543* (2006.01)
*G01N 27/327* (2006.01)
*G01N 33/20* (2019.01)

(52) U.S. Cl.
CPC ... *G01N 33/54346* (2013.01); *G01N 27/3275* (2013.01); *G01N 33/20* (2013.01); *G01N 33/5438* (2013.01)

(58) Field of Classification Search
CPC ......... G01N 33/54346; G01N 27/3275; G01N 33/20; G01N 33/5438
See application file for complete search history.

(56) References Cited

U.S. PATENT DOCUMENTS 7,591,938 B2 * 9/2009 Barlag ............... G01N 33/5438
204/411

FOREIGN PATENT DOCUMENTS

WO    2009/068862 A1    6/2009
WO    2015/042200 A1    3/2015

OTHER PUBLICATIONS

Shoup, et al., "Chronoamperometric Current at Finite Disk Electrodes", J. Electroanal. Chem., 140, Netherlands, 1982, pp. 237-245.

(Continued)

*Primary Examiner* — John McGuirk
(74) *Attorney, Agent, or Firm* — Grossman, Tucker, Perreault & Pfleger, PLLC

(57) ABSTRACT

The invention relates to a method for sensing target molecules in an analyte solution, a sensor for sensing target molecules in an analyte solution and a measurement system for sensing target molecules in an analyte solution. The method comprises providing a capture surface, wherein a plurality of capture molecules are arranged on the capture surface, each of the capture molecules being configured to bind to at least one of said target molecules. The method (Continued)

Figure 1A:
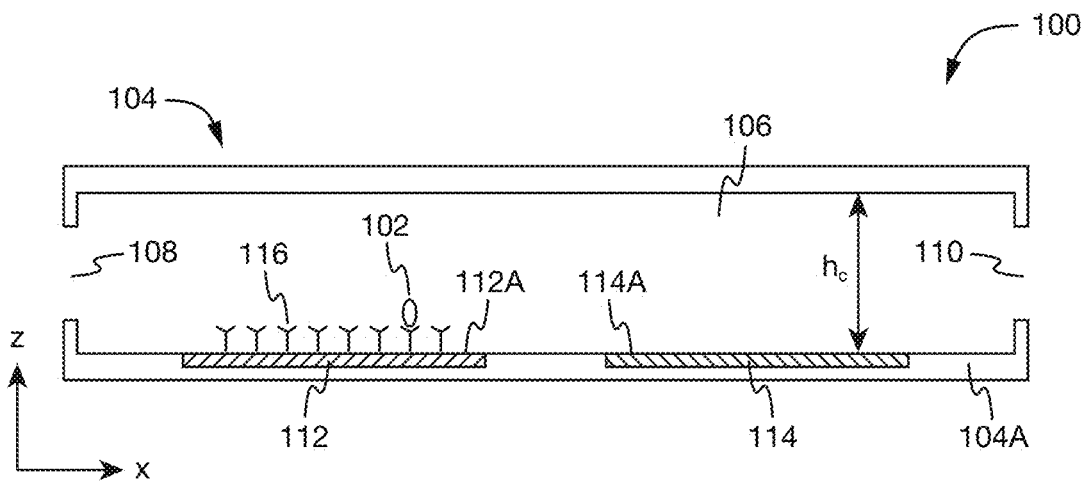

further comprises exposing the capture surface to the analyte solution to allow target molecules to bind to the capture molecules arranged on the capture surface. The capture surface is then exposed to a solution containing detection molecules, wherein each of the detection molecules contains an electrochemically active nanoparticle and is configured to bind to one of said target molecules bound to a capture molecule, thereby allowing said electrochemically active nanoparticles to bind to the capture surface through formation of a bond between the respective detection molecule comprising said nanoparticle and one of said target molecules bound to one of said capture molecules arranged on the capture surface. The method further comprises releasing nanoparticles that are bound to the capture surface and, after releasing said nanoparticles from the capture surface, determining an electrical signal at a detection electrode caused by electrochemical reactions of said nanoparticles released from the capture surface.

5 Claims, 7 Drawing Sheets

(56) References Cited

OTHER PUBLICATIONS

Robinson, et al., "Collision Dynamics during the Electrooxidation of Individual Silver Nanoparticles", J. Am. Chem. Soc. 139, ACS Publications, 2017, pp. 16923-16931.

Stuart, et al., "Determining Unknown Concentrations of Nanoparticles: The Particle-Impact Electrochemistry of Nickel and Silver", RCS Advances, 2, 2012, pp. 6879-6884.

Albrecht, et al., "Electrochemistry of Single Nanoparticles: General Discussion", Faraday Discuss, 2016, pp. 193 & 387.

Krause, et al., "Influence of Self-Assembled Alkanethiol Monolayers on Stochastic Amperometric On-Chip Detection of Silver Nanoparticles", Analytical Chemistry, 88, 2016, pp. 3632-3637.

Tschulik, et. al., "Non-Invasive Proving of Nanoparticle Electrostatics", ChemElectroChem, 2, 2015, pp. 112-118.

Figueiredo, et al., "On-Chip Stochastic Detection of Silver Nanoparticles without a Reference Electrode", ACS Sens, 3, 2018, pp. 93-98.

Little, "Particle-Electrode Impacts: Evidencing Partial Versus Complete Oxidation via Variable Temperature Studies", Journal of Electroanalytical Chemistry, 823, 2018, pp. 492-498.

Anderson, et al., "Single-Nanoparticle Electrochemistry through Immobilization and Collision", Acc. Chem. Res, 49, ACS Publications, 2016, pp. 2625-2631.

Krause, et al., "Stochastic On-Chip Detection of Subpicomolar Concentrations of Silver Nanoparticles", Anal. Chem, 87, ACS Publications, 2015, pp. 7321-7325.

Krause, et al., "The Influence of Supporting Ions on the Electrochemical Detection of Individual Silver Nanoparticles: Understanding the Shape and Frequency of Current Transients in Nano-Impacts", Chem. Eur. J. 23, 2017, pp. 1-7.

Toh, et al., "The Influence of the Capping Agent on the Oxidation of Silver Nanoparticles: Nano-Impacts vs Stripping Voltammetry", Wiley-VCH, 2015, 8 pages.

Ellison, et al., "The Use of Cylindrical Micro-Wire Electrodes for Nano-Impact Experiments; Facilitating the Sub-Picomolar Detection of Single Nanoparticles", Sensors and Actuators B 200, Elsevier, 2014, pp. 47-52.

Kang, et al., "Time-Resolved Detection and Analysis of Single Nanoparticle Electrocatalytic Impacts", J. Am. Chem. Soc., 137, ACS Publications, 2015, pp. 10902-10905.

Saw, et al., "Time-Resolved Impact Electrochemistry for Quantitative Measurement of Single-Nanoparticle Reaction Kinetics", Nano Res., 10(11), 2017, pp. 3680-3689.

Lai, et al., "Ultrasensitive Multiplexed Immunoassay with Electrochemical Stripping Analysis of Silver Nanoparticles Catalytically Deposited by Gold Nanoparticles and Enzymatic Reaction", Anal. Chem., 83, ACS Publications, 2011, pp. 2726-2732.

International Search Report and Written Opinion from corresponding PCT Appln. No. PCT/EP2021/050793, mailed Apr. 13, 2021. 19 pages.

Alba Iglesias-Mayor et al, "Nanoparticles as Emerging Labels in Electrochemical Immunosensors", Sensors, vol. 19, No. 23, Nov. 23, 2019, 28 pages.

Kanokwan Charoenkitamorn et al., "Electrochemical Immunoassay Using Open Circuit Potential Detection Labeled by Platinum Nanoparticles", Sensors, vol. 18, No. 2, Feb. 3, 2018, 12 pages.

Sharafeldin Mohamed et al, "Fe304nanoparticles on Graphene Oxide Sheets for Isolation and Ultrasensitive Amperometric Detection of Cancer Biomarker Proteins", Biosensors and Bioelectronics, Elsevier Science Ltd., Amsterdam, NL, vol. 91, Dec. 27, 2016. 8 pages.

* cited by examiner

SENSING OF MOLECULES BY ELECTROCHEMICAL DETECTION OF NANOPARTICLES

FIELD OF THE INVENTION

The present invention is in the field of chemical analysis and medical diagnostics. In particular, the invention relates to a sensor for sensing molecules by electrochemical detection of nanoparticles.

BACKGROUND

A large number of applications in fields ranging from chemical analysis over environmental testing to medical diagnostics rely on the detection and quantification of chemical substances. For these purposes, different types of sensors are used, which typically involve a transducing mechanism for converting a concentration of a target substance into a readily measurable quantity. A well-known example for this is the labeling of substances such as proteins with fluorescent markers, which allows for determining a number or concentration of such molecules by optical means. Similar techniques have been implemented using magnetic or electrochemically active labels and substances, for the latter see e.g. D. Grieshaber et al., Sensor 8(3), 1400 (2008) and J. Ronkainen et al., *Chem. Soc. Rev.* 39(5), 1747 (2010)

Another commonly used type of sensor are immunoassays such as western blots or enzyme-linked immunosorbent assays (ELISAs). In an ELISA, capture antibodies configured to selectively bind to a specific antigen are coated onto a substrate and exposed to an analyte solution such that target molecules in the analyte solution comprising the respective antigen may be captured by the antibodies. Subsequently, a second type of antibodies is provided, each of which is linked to an enzyme and also configured to bind to the target molecules. Thereby, the enzymes may be immobilized on the substrate in the form of sandwich structures containing a target molecule bound between two antibodies. Finally, the chemical substrate of the enzyme is added, triggering a chemical reaction whose product may for example be detected by optical or electrochemical means, see e.g. G. Lai et al., *Anal. Chem.* 83, 2726 (2011).

WO 2009/068862 A1 discloses a method for determining the presence or amount of a metal-labelled analyte in a sample. The method comprises adding a release agent to the metal labelled analyte to release the metal label from the analyte, the release agent forming a charged stable species with the metal label, applying a potential to bring the charged stable species to an electrode, dissolving the charged stable species under a positive potential to form metal ions, and carrying out a quantitative determination procedure such as anodic stripping voltammetry to determine the presence or amount of the metal-labelled analyte.

WO 2015/042200 A1 describes a device for sequencing protein samples comprising a channel with a plurality of nanogap electrodes and a computer processor that is programmed to measure nanocurrents between pairs of nanogap electrodes to identify monomers in a biomolecule.

The aforementioned techniques, however, often require complex procedures and laboratory equipment, e.g. for the fluorescent labeling of molecules or to ensure well-controlled and reproducible reaction conditions for the enzyme reaction in ELISAs. The reliability of ELISAs may furthermore be limited by non-specific adsorption of the enzyme-linked antibodies. These issues may prevent the use of the aforementioned techniques for applications requiring a fast and low-cost detection or quantification of target molecules with high sensitivity.

SUMMARY OF THE INVENTION

The object of the invention is thus to enable a simple and cost-efficient, yet reliable and precise sensing of target molecules in an analyte solution.

This object is met by a method for sensing target molecules in an analyte solution, a sensor for sensing target molecules in an analyte solution, and a measurement system for sensing target molecules in an analyte solution. Embodiments of the present invention are detailed in the dependent claims.

The method for sensing target molecules in an analyte solution according to the invention comprises (1) providing a capture surface. A plurality of capture molecules are arranged on the capture surface, wherein each of the capture molecules is configured to bind to at least one of said target molecules. The method further comprises (2) exposing the capture surface to the analyte solution to allow target molecules to bind to the capture molecules arranged on the capture surface. The method also comprises (3) exposing the capture surface to a solution containing detection molecules. Each of the detection molecules contains an electrochemically active nanoparticle. Furthermore, each of the detection molecules is configured to bind to one of said target molecules bound to a capture molecule. This hence allows said electrochemically active nanoparticles to bind to the capture surface through formation of a bond between the respective detection molecule comprising said nanoparticle and one of said target molecules bound to one of said capture molecules arranged on the capture surface. The method also comprises (4) releasing nanoparticles that are bound to the capture surface and (5) determining an electrical signal at a detection electrode after releasing said nanoparticles from the capture surface, wherein the electrical signal is caused by electrochemical reactions of said nanoparticles released from the capture surface.

The capture surface may for example be provided as part of a sensor, e.g. a sensor in accordance with an embodiment of the invention as detailed below. The detection electrode may be provided together with the capture surface, e.g. as part of the same sensor. In some examples, the capture surface may be a surface of the detection electrode. In other embodiments, the capture surface may be a surface separate from the detection electrode, e.g. as detailed below. The capture surface and detection electrode may be exposed to a measurement volume, e.g. to an inner volume of a measurement chamber, such that the capture surface and a surface of the detection electrode come in contact with a fluid filling the measurement volume. The capture surface may comprise or consist of a conducting material, e.g. a metal, a metal alloy, a conducting polymer material and/or a conducting carbon material such as graphite and/or glassy carbon. Additionally or alternatively, the capture surface may comprise or consist of an insulating material, e.g. polystyrene, polypropylene and/or polycarbonate. The detection electrode may comprise or consist of a conducting material, in particular a metal, a metal alloy, a conducting polymer material and/or a conducting carbon material such as graphite and/or glassy carbon.

The capture molecules may be adsorbed on the capture surface by chemisorption, e.g. through a chemical bond between a first functional group of each of the capture molecules and the capture surface. The capture molecules may be arranged on the capture surface in one or more layers. Each of the capture molecules may comprise a second functional group that is configured to form a chemical bond with one of the target molecules, e.g. with a first binding site on the respective target molecule. In some embodiments, each of the capture molecules may comprise a plurality of second functional groups, each of which is configured to form a chemical bond with one of the target molecules.

The capture surface may for example be exposed to the analyte solution by filling the analyte solution into the measurement volume. The analyte solution may e.g. be a medical sample such as a blood sample, an environmental sample such as a water sample, or a chemical sample such as a product of a chemical process. Accordingly, the target molecules may be a chemical substance, e.g. a toxic substance, a pollutant or a reaction product. The target molecules may also be biomolecules, in particular disease biomarkers, such as hormones, neurotransmitter, metabolites, proteins, DNA molecules, RNA molecules, bacteria or viruses.

By exposing the capture surface to the analyte solution, target molecules contained in the analyte solution may bind to capture molecules arranged on the capture surface, thereby immobilizing the target molecules on the capture surface. The capture surface may be exposed to the analyte solution for a first incubation time. The first incubation time may be chosen based on reaction kinetics of the binding reaction between the target molecules and the capture molecules, a concentration of capture molecules on the capture surface, an expected concentration of target molecules in the analyte solution, and/or diffusion properties of the target molecules in the analyte solution. In some embodiments, the analyte solution may be diluted prior to exposing the capture surface to the analyte solution. Exposing the capture surface to the analyte solution may also comprise generating a flow of the analyte solution, e.g. to direct the analyte solution towards the capture surface.

Subsequently, the capture surface is exposed to the solution containing the detection molecules. Each of the detection molecules may for example contain a functional group that is configured to form a chemical bond with one of the target molecules, e.g. with a second binding site on the respective target molecule. The second binding site is different from the first binding site, to which the second functional group of the capture molecules is configured to bind. Detection molecules from the solution may thus bind to the capture surface via target molecules immobilized on the capture surface by the capture molecules, i.e. by forming a sandwich structure consisting of a capture molecule arranged on the capture surface, a target molecule bound to the capture molecule and a detection molecule bound to the target molecule. Detection molecules that do not bind to the capture molecules on the capture surface may subsequently be removed, e.g. by rinsing the capture surface with a solution that does not contain detection molecules, for example a buffer solution or a measurement solution (see below).

The capture surface may be exposed to the solution containing the detection molecules for a second incubation time. The second incubation time may be chosen based on reaction kinetics of the binding reaction between the target molecules and the detection molecules, a concentration of detection molecules in the solution, an expected concentration of target molecules on the capture surface, and/or diffusion properties of the detection molecules in the solution. Preferably, a concentration of detection molecules in the solution and/or the second incubation time are chosen to be sufficiently large such that at least 90%, preferably at least 95% of target molecules immobilized on the capture surface bind to one of the detection molecules.

Each of the detection molecules contains an electrochemically active nanoparticle. The electrochemically active nanoparticle may for example be bound to the functional group of the respective detection molecule through a direct chemical bond or through a linker element. In the context of this disclosure, the term "electrochemically active nanoparticle" refers to a nanoparticle that is configured to undergo a chemical reaction with one or more other substances, wherein the chemical reaction involves the release or absorption of one or more free charged particles, in particular free electrons, e.g. to or from an electrode such as the detection electrode as detailed below. Accordingly, a surface of each of the electrochemically active nanoparticles may for example comprise one or more electrochemically active groups configured to undergo a corresponding chemical reaction, e.g. as described in more detail below.

After exposing the capture surface to the solution containing the detection molecules, nanoparticles that are bound to the capture surface are released from the capture surface. This may comprise breaking the bonds between the nanoparticles and remaining parts of the respective detection molecules and/or breaking the bonds between the capture molecules and the capture surface, e.g. by electrically, electrochemically, chemically, optically, mechanically, and/or thermally induced dissociation. Prior to releasing the nanoparticles from the capture surface, a measurement solution may be provided, wherein the measurement solution initially does not contain any detection molecules and/or free nanoparticles. The measurement solution may e.g. be an electrolyte solution as detailed below.

Subsequently, an electrical signal is determined at the detection electrode, wherein the electrical signal may for example be a current through the detection electrode or a voltage at the detection electrode as a function of time. Determining the electrical signal may e.g. comprise determining a digital or analog measurement signal characterizing the electrical signal, in particular characterizing an amplitude of the electrical signal as a function of time. The electrical signal is at least in part caused by electrochemical reactions of the nanoparticles released from the capture surface, e.g. by the release or absorption of free electrons to/from the detection electrode as a result of the electrochemical reaction. The electrochemical reaction may in particular take place in the vicinity of the detection electrode, for example during impact of the respective nanoparticle on the detection electrode as detailed below. In some examples, the detection electrode may comprise a plurality of microelectrodes. Determining the electrical signal may comprise determining a signal at each of the microelectrodes independently and combining the microelectrode signals to obtain the electrical signal at the detection electrode. In other examples, each of the microelectrode signals may be analyzed independently, e.g. similar as described below for the electrical signal at the detection electrode.

The method according to the invention combines advantages of ELISA methods such as a high sensitivity and molecule-specific detection with the simplicity of an electrical measurement. In contrast to conventional electrochemical immunoassays as e.g. described in G. Lai et al., *Anal. Chem.* 83, 2726 (2011), the electrical detection may be spatially separated from the immobilization of target and detection molecules, with the former being performed with the detection electrode while the latter takes place on the capture surface, which may be separate from the detection electrode. Nanoparticles bound to the capture surface may be released in a controlled fashion, e.g. by applying a dissociation voltage to an electrode comprising the capture surface, and may subsequently interact with the detection electrode. This improves the robustness with regard to false-positive counts, which may arise due to a non-specific binding of detection molecules to binding sites other than the immobilized target molecules. In addition, the determination of the electrical signal is temporally separated from the release of the nanoparticles. Furthermore, the electrochemical reaction of the nanoparticles may be less sensitive to changes in reaction conditions, e.g. a change in temperature, than enzymatic reactions. As detailed in the following, nanoparticles may be detected on a single-particle level, thus enabling a high sensitivity and precise determination of a concentration of target molecules in the analyte solution.

In some examples, the capture surface may be a surface of an electrode, in particular a surface of a capture electrode separate from the detection electrode. Releasing the nanoparticles from the capture surface may comprise applying a voltage to the electrode comprising the capture surface to release the nanoparticles by electrically and/or electrochemically induced dissociation. The voltage may e.g. be applied relative to a reference electrode exposed to the measurement volume or relative to a reference electrode on chip, for example a reference electrode integrated into a microfluidic chip. An amplitude of the applied voltage and/or a duration for which the voltage is applied may be chosen to be sufficiently large to break the bonds between the nanoparticles and the remaining parts of the respective detection molecules and/or to break the bonds between capture molecules and the capture surface. The dissociation voltage may e.g. be in the range between –2 V and +2 V versus a saturated silver/silver chloride reference electrode potential and may for example be applied for a duration between 1 μs to 1 s. In some examples, nanoparticles released from the capture surface may be charged, which may e.g. allow for controlling the motion of the released nanoparticles by application of an electric field.

Additionally or alternatively, the nanoparticles that are bound to the capture surface may be released by chemically, optically, mechanically, and/or thermally induced dissociation. In some embodiments, releasing the nanoparticles from the capture surface comprises exposing the capture surface to a dissociation solution to release the nanoparticles by chemically induced dissociation. The dissociation solution may e.g. be the measurement solution or may be added to the measurement solution. The dissociation solution may for example comprise a dissociating agent that is configured to break the bonds between the nanoparticles and the remaining parts of the respective detection molecules and/or to break the bonds between the capture molecules and the capture surface, e.g. by acting as a catalyst for a corresponding chemical dissociation reaction. In another example, ultrasound may be used to release the nanoparticles by mechanically induced dissociation.

In a preferred embodiment, an electrolyte solution may be provided as a measurement solution for determining the electrical signal. The electrolyte solution may contain ions that are configured to undergo a chemical reaction with one of the nanoparticles, wherein the chemical reaction involves the release or absorption of a free electron. The electrolyte solution may for example contain one or more types of ions selected from the group consisting of chloride ($Cl^-$), bromide ($Br^-$), iodide ($I^-$), nitrate ($NO_3$) and sulfate ($SO_4^{2-}$).

In some embodiments, the capture surface is spatially separated from the detection electrode. The detection electrode may for example be arranged adjacent to one or more edges of the capture surface. In some examples, a flow of the measurement solution, e.g. the electrolyte solution, may be generated from the capture surface towards the detection electrode. Thereby, nanoparticles released from the capture surface may for example be transported towards the detection electrode by advection and/or diffusion of the nanoparticles, which may be limited to a small diffusion layer due to the advection. This may increase the probability for nanoparticles released from the capture surface to reach the vicinity of the detection electrode and thus interact with the detection electrode.

The method may further comprise rinsing the capture surface and/or the detection electrode with a buffer solution. In particular, the capture surface and/or the detection electrode may be rinsed with the buffer solution after exposing the capture surface to the solution containing the detection molecules and prior to releasing the nanoparticles from the capture surface. This may be advantageous to reduce non-specific adsorption and to ensure that only nanoparticles released from the capture surface interact with the detection electrode while determining the electrical signal. In one example, only the detection electrode may be rinsed, e.g. to avoid inadvertently removing nanoparticles bound to capture surface.

In some examples, providing the capture surface may comprise arranging capture molecules on the capture surface. In other words, the capture surface may initially be provided as a bare surface without any capture molecules arranged thereon and may subsequently be functionalized by depositing capture molecules on the capture surface. Providing the capture surface may in particular comprise adsorbing capture molecules on the capture surface by chemisorption, e.g. by exposing the capture surface to a solution containing the capture molecules to allow capture molecules to bind to the capture surface. Each of the capture molecules may contain a first functional group configured to form a chemical bond with the capture surface. In a preferred embodiment, the capture surface may consist of or comprise a metal and each of the capture molecules may contain a sulfur group, e.g. a thiol or a disulfide, that is configured to form a chemical bond with the metal of the capture surface.

In a preferred embodiment, each of the capture molecules contains an aptamer or antibody that is configured to bind to one of the target molecules, e.g. to a corresponding first antigen on the surface of the respective target molecule. Similarly, each of the detection molecules may contain an aptamer or antibody that is configured to bind to one of the target molecules, e.g. to a corresponding second antigen on the surface of the respective molecule. Using aptamers and/or antibodies may allow for creating highly-selective capture and/or detection molecules for a large variety of biomolecules. The respective antibody may for example be an immunoglobulin G or a part thereof, e.g. may be derived from an immunoglobulin G.

Preferably, the nanoparticles are metal nanoparticles, i.e. consist of or contain metal. The nanoparticles may in particular consist of or contain one or more metals selected from the group consisting of silver, copper, gold and platinum. Metallic atoms on the surface of the nanoparticles may e.g. undergo an oxidation reaction with negatively charged ions of an electrolyte solution in the vicinity of the detection electrode, thereby causing a transfer of electrons to the detection electrode. Preferably, the detection electrode comprises or consists of a material different from the metal of the metal nanoparticles, e.g. to prevent electrochemical reactions of the surface of detection electrode exposed to the measurement solution.

In some examples, the nanoparticles may be composite nanoparticles comprising a core surrounded by a surface layer. The surface layer may for example consist of or comprise metal, e.g. one or more metals selected from the group consisting of silver, copper, gold and platinum. The core may for example consist of or comprise a ferromagnetic or ferrimagnetic material such as iron, cobalt, nickel and/or iron oxide. This may allow for employing a magnetic field to control the nanoparticles, e.g. to control a motion of the nanoparticles after release from the capture surface.

In a preferred embodiment, determining the electrical signal at the detection electrode comprises applying a bias voltage to the detection electrode and measuring the current through the detection electrode. The bias voltage may for example be applied between the detection electrode and a reference electrode in contact with the measurement solution or a reference electrode on chip. A voltage at the detection electrode may facilitate or suppress the electrochemical reaction of the nanoparticles and may influence additional contributions to the electrical signal such as an electrolyte current. Applying the bias voltage may thus facilitate the determination and analysis of the electrical signal.

Preferably, the method further comprises a step of detecting impact events in the electrical signal. An impact event is a feature in the electrical signal that is caused by an electrochemical reaction during impact of one of the nanoparticles released from the capture surface on the detection electrode. The electrochemical reaction may for example lead to the release or absorption of electrons to/from the detection electrode and the impact of a nanoparticle may thus generate a transient current spike. Accordingly, an impact of a nanoparticle on the detection electrode is to be understood as the nanoparticle coming close enough to the detection electrode for the electrochemical reaction to take place, which may or may not involve direct contact with the detection electrode. The detection of silver nanoparticles in an electrolyte solution with single-particle sensitivity has for example been reported in K. J. Krause et al., *Anal. Chem.* 87, 7321 (2015), see also K. J. Krause et al., *Anal. Chem.* 88, 3532 (2016) and P. G. Figueiredo et al., *ACS Sens.* 3, 93 (2018).

Impact events may for example be detected by comparing the electrical signal to one or more pre-determined threshold values. Additionally or alternatively, this may comprise determining a time-integrated amplitude and/or a duration of a spike, each of which may be compared with one or more pre-determined threshold values. Detecting impact events may also comprise comparing a shape of a spike to a reference shape, e.g. to determine if the respective spike is compatible with the impact of a nanoparticle.

Preferably, the method also comprises determining a concentration of target molecules in the analyte solution based on the electrical signal. The concentration may for example be determined by determining an average current through the detection electrode, which may depend on a number of nanoparticles in the measurement solution and thus on a number of target molecules immobilized on the capture surface. In a preferred embodiment, the concentration is determined by determining a number or frequency of impact events in the electrical signal, which also may depend on a number of nanoparticles in the measurement solution and thus on a number of target molecules immobilized on the capture surface. The concentration of target molecules may for example be obtained by using a predetermined calibration curve associating a number or frequency of impact events with a concentration of target molecules.

In some examples, the analyte solution may contain two or more different kinds of target molecules. The target molecules may for example comprise target molecules of a first kind and target molecules of a second kind. The method may comprise providing two or more capture surfaces, wherein different types of capture molecules are arranged on respective capture surfaces. The capture surfaces may for example be surfaces of respective capture electrodes. The method may for example comprise providing a first capture surface and a second capture surface, wherein a plurality of capture molecules of a first kind are arranged on the first capture surface and a plurality of capture molecules of a second kind are arranged on the second capture surface. Each of the capture molecules of the first kind may e.g. be configured to bind to at least one of the target molecules of the first kind, but not to target molecules of the second kind. Each of the capture molecules of the second kind may e.g. be configured to bind to at least one of the target molecules of the second kind, but not to target molecules of the first kind.

The method may further comprise exposing each of the capture surfaces to the analyte solution and exposing each of the capture surfaces to a solution containing detection molecules. Each of the detection molecules may contain an electrochemically active nanoparticle and may be configured to either bind to one of the target molecules of the first kind bound to a capture molecule of the first kind or to one of the target molecules of the second kind bound to a capture molecule of the second kind. In other examples, the detection molecules may comprise different kinds of detection molecules, e.g. detection molecules of the first kind configured to bind to target molecules of the first kind bound to a capture molecule of the first kind and detection molecules of a second kind configured to bind to a target molecule of the second kind bound to a capture molecule of the second kind.

The method may further comprise releasing nanoparticles bound to the capture surfaces and determining one or more electrical signals at the detection electrode. Preferably, the nanoparticles are released from the capture surfaces sequentially and an electrical signal at the detection electrode is determined for each of the capture surfaces individually. For example, nanoparticles that are bound to the first capture surface may be released in a first step and an electrical signal at the detection electrode caused by electrochemical reactions of the nanoparticles released from the first capture surface may be determined. Subsequently, in a second step, nanoparticles that are bound to the second capture surface may be released and an electrical signal at the detection electrode caused by electrochemical reactions of the nanoparticles released from the second capture surface may be determined. The measurement volume may be rinsed after releasing nanoparticles from the first capture surface and after determining the electrical signal associated with nanoparticles released from the first capture surface, but prior to releasing nanoparticles from the second capture surface and prior to determining the electrical signal associate with nanoparticles released from the second capture surface. The method may further comprise analyzing the electrical signals, e.g. to detect impact events and/or concentrations of target molecules as described above.

The above method may further be generalized to an arbitrary number of types of target molecules in the analyte by using a corresponding number of capture surfaces and types of capture molecules.

Additionally or alternatively, target particles of different kinds may also be detected using a single capture surface, e.g. a single capture electrode, as described in the following. The target molecules may for example comprise target molecules of a first kind and target molecules of a second kind. The detection molecules may comprise detection molecules of a first kind, each of which is e.g. configured to bind to one of the target molecules of the first kind, but not to target molecules of the second kind. The detection molecules may further comprise detection molecules of a second kind, each of which is e.g. configured to bind to one of the target molecules of the second kind, but not to target molecules of the first kind. Each of the detection molecules of the first kind may contain a nanoparticle of a first kind, e.g. a metal nanoparticle of a first kind. Each of the detection molecules of the second kind may contain a nanoparticle of a second kind, e.g. a metal nanoparticle of a second kind.

The nanoparticles of the first and second kind may be configured to generate impact events in the electrical signal that are distinguishable from one another. For this, nanoparticles of the first and second kind may for example be configured to undergo different chemical reactions and/or may comprise different numbers of electrochemically active groups participating in the chemical reaction. A charge transferred to the detection electrode during impact of a nanoparticle of the first kind may be larger or smaller than a charge transferred to the detection electrode during impact of a nanoparticle of the second kind. The charge may e.g. be the average charge that is transferred during impact of the respective nanoparticle or may be the maximum charge that is transferred when every electrochemically active group on the surface of the respective nanoparticle undergoes an electrochemical reaction. In some embodiments, the transferred charge for a nanoparticle of the first kind may for example be at least 20% larger, preferably at least 50% larger than the transferred charge for a nanoparticle of the second kind.

Nanoparticles of the first and second kind may for example differ in their surface area and/or in their volume. A surface area of the nanoparticles of the first kind may for example be larger or smaller than a surface area of the nanoparticles of the second kind, e.g. at least 20% larger, preferably at least 50% larger than the surface area of the nanoparticles of the second kind. Thereby, a difference in the transferred charge may for example be achieved for nanoparticles comprising or consisting of a material that may only or predominantly undergo an electrochemical reaction at its surface during impact, e.g. gold. Additionally or alternatively, a volume of the nanoparticles of the first kind may for example be larger or smaller than a volume of the nanoparticles of the second kind, e.g. at least 20% larger, preferably at least 50% larger than the volume of the nanoparticles of the second kind. Thereby, a difference in the transferred charge may for example be achieved for nanoparticles comprising or consisting of a material that may undergo an electrochemical reaction throughout its entire volume during impact, i.e. at its surface and in its interior or core, for example silver. In another example, nanoparticles of the first kind may comprise or consist of a first metal and nanoparticles of the second kind may comprise or consist of a second metal different from the first metal.

The method may further comprise associating the impact events in the electrical signal with nanoparticles of the first kind or with nanoparticles the second kind. The impact events may for example be distinguished based on their amplitude, e.g. their peak amplitude or their time-integrated amplitude, their duration and/or their shape. Thereby, a number or frequency of impact events may be determined independently for each kind of target molecule using a single capture surface.

The invention further relates to a sensor for sensing target molecules in an analyte solution. The sensor comprises a measurement chamber having an inlet and an outlet. The sensor further includes a capture surface that is exposed to an inner volume of the measurement chamber. A plurality of capture molecules are arranged on the capture surface, each of the capture molecules being configured to bind to at least one of said target molecules. The sensor comprises a detection electrode having a detection surface exposed to the inner volume of the measurement chamber. An inner height $h_c$ of the measurement chamber perpendicular to the detection surface is less than 30% of a length of the detection surface along a flow path from the capture surface to the outlet of the measurement chamber. In addition, the sensor includes an electrical connector or connection assembly configured to provide an electrical connection to the detection electrode.

The sensor is configured for use with a method according to an embodiment of the invention as described above. Accordingly, the sensor allows for the detection of target molecules in the analyte solution with a high sensitivity as well as for a precise determination of the concentration of target molecules in the analyte solution.

The measurement chamber may for example consist of or comprise a glass or a polymer material. The capture surface and the detection electrode may for example be arranged on or embedded in a wall of the measurement chamber such that each of the capture and detection surfaces comes in contact with a fluid filling the measurement chamber. In some examples, the capture surface may also be the detection surface or a part thereof or may comprise the detection surface. The capture surface may e.g. be a center portion of the detection surface that is surrounded by an outer portion of the detection surface. In other embodiments, the capture surface may be separate from the detection surface and/or from the detection electrode. In one example, the capture surface may e.g. be a surface of a wall of the measurement chamber or a part thereof. The capture surface may in particular be a surface of a capture electrode separate from the detection electrode. The electrical connector or connection assembly may be configured to provide independent electrical connections to the capture electrode and to the detection electrode.

The capture surface may for example comprise or consist of a conducting material, e.g. a metal such as gold and/or platinum, a metal alloy, a conducting polymer material and/or a conducting carbon material such as graphite and/or glassy carbon. Additionally or alternatively, the capture surface may comprise or consist of an insulating material, e.g. polystyrene, polypropylene and/or polycarbonate. The detection electrode comprises or consists of a conducting material, in particular a metal such as gold and/or platinum, a metal alloy, a conductive polymer material and/or a conducting carbon material such as graphite and/or glassy carbon. The detection electrode may comprise additional layers underneath the detection surface. The detection electrode may for example comprise a substrate which may e.g. comprise or consist of glass, quartz, polyethylene terephthalate (PET), polyethylene naphthalate (PEN), polyimide, parylene, polydimethylsiloxane (PDMS), polyethylene glycol diacrylate (PEGDA), other insulating polymers or a combination thereof. In some example, the detection electrode may also comprise an adhesion layer, which may e.g. comprise or consist of titanium, chromium or a combination thereof. Additionally or alternatively, additional layers may also be arranged underneath the capture surface, e.g. as part of the capture electrode.

The measurement chamber may e.g. be a microfluidic chamber, wherein at least one of a height and a width of the inner volume enclosed by the measurement chamber, may be smaller than 1 mm, preferably smaller than 100 μm. The height is measured perpendicular to the detection surface. The width is measured parallel to the detection surface and perpendicular to a main flow path connecting the inlet of the measurement chamber to the outlet of the measurement chamber. The main flow path is the path along which a fluid flows from the inlet to the outlet. Preferably, the detection electrode is arranged downstream of the capture surface along the main flow path. A length of the inner volume between the inlet and the outlet may for example be smaller than 200 mm, in some examples smaller than 1 mm. The measurement chamber may for example be a microfluidic channel, which may be in fluid communication with a microfluidic structure. The microfluidic structure may comprise additional elements such as a reservoir, a pump, a valve, and/or connectors for providing and extracting the analyte solution. The pump may e.g. be configured to generate a controlled flow through the measurement chamber. In the context of this disclosure, the height, width and length of the inner volume of the measurement chamber may also be referred to as the inner height, the inner width, and the inner length of the measurement chamber, respectively.

The inner height of the measurement chamber perpendicular to the detection surface is less than 30% of a length of the detection surface along a flow path from the capture surface to the outlet of the measurement chamber, which may also be referred to as the release flow path in the following. The release flow path is the path along which a fluid flows from the center of the capture surface to the outlet when generating a flow from the inlet to the outlet. Accordingly, the release flow path may correspond to a portion of the main flow path. If the capture surface corresponds to the detection surface or a part thereof, the length of the detection surface along the release flow path may e.g. be the respective length measured from the center of the capture surface to the edge of the detection surface that is closest to the outlet. A small inner height of the measurement chamber may increase a probability of particles diffusing through the inner volume to interact with the detection surface. Preferably, the inner height of the measurement chamber perpendicular to the detection surface is less than 20%, in some embodiments less than 10% of the length of the detection surface along the release flow path. In some examples, the inner height of the measurement chamber perpendicular to the detection surface may be less than 30 μm, preferably less than 10 μm.

In a preferred embodiment, a width of the detection surface perpendicular to the release flow path is at least 75%, preferably at least 90% of the inner width of the measurement chamber perpendicular to the release flow path. In some examples, the detection surface may extend over the entire inner width of the measurement chamber, i.e. the width of the detection surface may be 100% of the inner width of measurement chamber. This may further increase the probability of particles diffusing through the volume to interact with the detection surface.

Each of the capture molecules may contain a first functional group forming a chemical bond with the capture surface. Each of the capture molecules may in particular contain a sulfur group, e.g. a disulfide or a thiol, forming a chemical bond with a metal on the capture surface. The capture molecules may for example be arranged on the capture surface in a monomolecular layer. In other examples, more than one layer of capture molecules may be arranged on the capture surface. The capture molecules may further comprise a second functional group configured to bind to one of the target molecules, e.g. as described above.

In a preferred embodiment, the detection electrode comprises an array of microelectrodes. The electrical connector or connection assembly may be configured to provide individual electrical connections to each of the microelectrodes, i.e. such that an electrical signal may be determined and/or applied at each of the detection electrodes independently. Each of the microelectrodes may for example have a surface area between 50 μm$^2$ and 1000 μm$^2$. Together, the surfaces of the microelectrodes form the detection surface. Preferably, the detection surface covers a surface area of more than 75%, in one example more than 90% of a surface area of the detection electrode exposed to the inner volume. The microelectrodes may be arranged in a periodic pattern or in an aperiodic pattern.

The sensor may further comprise a support electrode that is exposed to the inner volume of the measurement chamber. The support electrode may for example be arranged between the capture surface and the detection electrode or may be arranged adjacent to the capture surface such that a distance between the capture surface and the detection electrode is similar to a distance between the support electrode and the detection electrode. In some examples, the capture surface is a surface of a first capture electrode and the support electrode forms a second capture electrode. A plurality of capture molecules may be arranged on the second capture electrode, for example capture molecules of a different kind than the capture molecules arranged on the first capture electrode, e.g. as described above. In other examples, the support electrode may be a guard electrode without any capture molecules arranged thereon. The electrical connector or connection assembly may be configured to provide an independent electrical connection to the support electrode.

The sensor may further comprise a reference electrode that is exposed to the inner volume of the measurement chamber. The electrical connector or connector assembly may be configured to provide an independent electrical connection to the reference electrode, e.g. such that the reference electrode may be used as a reference point for applying a voltage to one of the other electrodes. The reference electrode may for example consist of or comprise a material with a stable electrochemical electrode potential. The reference electrode may in particular be a silver silver/chloride electrode (Ag/AgCl) or a pseudo reference electrode comprising or consisting of platinum and/or gold.

In a preferred embodiment, the capture surface comprises an anti-adsorption coating. The anti-adsorption coating may for example be configured to prevent direct adsorption of target molecules and/or detection molecules on the capture surface. The anti-adsorption coating may e.g. consist of or comprise polyethylene glycol and/or perfluorinated polymers. The anti-adsorption coating may for example be a self-assembled monolayer.

In some examples, the capture electrode and/or the capture surface comprises or consists of a first material, e.g. a first metal, preferably gold, and the detection electrode and/or detection surface comprises or consists of a second material different from the first material, e.g. a second metal different from the first metal, preferably platinum.

In some embodiments, the sensor may comprise more than one detection electrode, for example a first detection electrode adjacent to one side of the capture surface and a second detection electrode adjacent to the opposing side of the capture surface. In other examples, the detection electrode may partially or completely surround the capture surface, wherein the capture surface may e.g. be arranged at the center of the detection electrode.

The invention further relates to a measurement system for sensing target molecules in an analyte solution. The measurement system is configured for use with a sensor comprising a capture surface and a detection electrode, e.g. a sensor in accordance with an embodiment of the invention as described above. Accordingly, the measurement system may for example be configured to be connected to the sensor via a cable or may be configured to receive the sensor, e.g. in a corresponding mount or slot, to provide an electrical connection with an electrical connector of the sensor.

The measurement system comprises an ammeter configured to measure a current through the detection electrode. The ammeter may in particular be a low-noise ammeter configured to measure a picoampere and/or nanoampere current through the detection electrode, for example to allow for detection of single nanoparticles, e.g. as described in A. Yakushenko et al., *Anal. Chem.* 85, 5483 (2012) and K. J. Krause et al., *Anal. Chem.* 87, 7321 (2015). The ammeter may comprise one or more amplifiers for amplifying a current through the detection electrode. Preferably, the ammeter has a plurality of independent channels, e.g. for independently measuring currents through a plurality of microelectrodes in the sensor.

The measurement system also comprises a controller for controlling the ammeter. The controller may be implemented in hardware, software, or a combination thereof. The controller may in particular comprise a microcontroller with a processor and a storage medium storing instructions to be executed by the processor to provide the functionality described in the following. The controller may be configured to execute at least some of the steps of embodiments of the method according to the invention described above. The ammeter and the controller may be integrated into a single device or may be independent units, which may e.g. be connected by cables and/or wireless communication links.

The controller is configured to initiate a dissociation process to release electrochemically active nanoparticles adsorbed on the capture surface. For this, the controller may for example be configured to control a voltage source for applying a dissociation voltage to an electrode comprising the capture surface to release the electrochemically active molecules by electrically and/or electrochemically induced dissociation as detailed below. Additionally or alternatively, the controller may e.g. be configured to expose the capture surface to a dissociation solution to release the electrochemically active molecules by chemically induced dissociation, e.g. by controlling a valve and/or pump for providing the dissociation solution and/or a dissociating agent. In other examples, the controller may also be configured to control a light source, an ultrasound source and/or a heating element for releasing the electrochemically active molecules.

The controller is further configured to determine a measurement signal characterizing the current through the detection electrode as a function of time using the ammeter after applying initiating the dissociation process. The measurement signal may for example be an analog or digital signal quantifying an amplitude of the current through the detection electrode, which may be read out from the ammeter by the controller. The controller may further be configured to initiate or terminate a measurement of the ammeter, e.g. by generating corresponding trigger signals.

The controller is also configured to determine a number of impact events from the measurement signal. An impact event is a feature in the measurement signal, e.g. a transient spike, that is caused by an electrochemical reaction during the impact of one of the nanoparticles released from the capture surface on the detection electrode. The controller may in particular determine the number of impact events by identifying spikes in the measurement signal as described above. For this, the controller may for example be configured to compare the measurement signal to one or more threshold values.

In some embodiments, the measurement system may comprise a voltage source and the controller may be configured to control the voltage source, e.g. by generating analog and/or digital control signals. The voltage source may be configured to apply a voltage to one or more electrodes, e.g. to the detection electrode and/or to a capture electrode comprising the capture surface. Preferably, the voltage source is configured to apply independent voltages to two or more electrodes of the sensor, e.g. at least the capture electrode and the detection electrode. The voltage source may in particular be configured to apply the voltage between the respective electrode and a reference electrode, wherein the reference electrode may for example be an internal reference electrode of the sensor or an external reference electrode of the measurement system.

Additionally or alternatively, the measurement system may be configured to be connected to an external voltage source providing the corresponding functionality, wherein the controller is configured to control the external voltage source accordingly. In a preferred embodiment, the voltage source is configured to apply a voltage to the detection electrode, e.g. between the detection electrode and the external or internal reference electrode, and the controller is configured to apply a bias voltage to the detection electrode via the voltage source while measuring the current through the detection electrode. For this, the controller may be configured to adjust an amplitude and/or a duration of a first voltage provided by the voltage source, e.g. by generating corresponding analog and/or digital signals such as control signals and/or trigger signals.

In some embodiments, the capture surface may be a surface of an electrode, e.g. a surface of the detection electrode or of a capture electrode separate from the detection electrode. Preferably, the voltage source is configured to apply a voltage to the electrode comprising the capture surface, e.g. relative to the external or internal reference electrode. The controller may be configured to initiate the dissociation process by applying a dissociation voltage to the electrode comprising the capture surface to release electrochemically active nanoparticles adsorbed on the capture surface by electrically and/or electrochemically induced dissociation. For this, the controller may be configured to adjust an amplitude and/or a duration of a second voltage provided by the voltage source, e.g. by generating corresponding analog and/or digital signals such as control signals and/or trigger signals.

The measurement system may further be configured to sense target molecules of different kinds in the analyte solution, e.g. as described above for the method according to the invention. In some examples, the capture surface is a first capture surface, e.g. a surface of a first capture electrode, and the sensor further comprises a second capture surface, e.g. a surface of a second capture electrode. The controller may be configured to first initiate a first dissociation process to release electrochemically active nanoparticles from the first capture surface, e.g. by applying a first dissociation voltage to the first capture electrode via the voltage source, and to determine a first measurement signal characterizing the current through the detection electrode, associated with nanoparticles released from the first capture electrode. The controller may further be configured to subsequently initiate a second dissociation process to release electrochemically active nanoparticles from the second capture surface, e.g. by applying a second dissociation voltage to the second capture electrode via the voltage source, and to determine a second measurement signal characterizing the current through the detection electrode, associated with nanoparticles released from the second capture electrode. The controller may further be configured to analyze the first and second measurement signals, e.g. to determine the number of impact events and/or the concentration of target molecules as described above.

In a preferred embodiment, the controller is configured to determine a parameter associated with an impacting nanoparticle, in particular a metal nanoparticle, from a corresponding impact event in the measurement signal. The controller may for example be configured to determine a charge transferred to the detection electrode during impact of the nanoparticle by determining an amplitude, in particular a time-integrated amplitude, of the measurement signal during the impact event. The controller may also be configured to determine a size of the nanoparticle by determining an amplitude and/or the time-integrated current associated with the impact event. For this, the controller may for example use a pre-determined calibration curve associating the time-integrated current with a size of the nanoparticle. In other examples, the controller may be configured to determine the size of the nanoparticle by determining whether the nanoparticle is a nanoparticle of a first kind or a nanoparticle of a second kind based on the time-integrated current, e.g. by comparing the time-integrated current to one or more threshold values.

In some examples, the measurement system may further comprise a sensor in accordance with an embodiment of the invention. Preferably, the measurement system is configured such that the sensor can be coupled removably to other elements of the measurement system, e.g. via a cable that can be connected and disconnected or through a corresponding mount for attaching the sensor, e.g. a slot that the sensor can be insert in and removed from.

The measurement system may comprise further elements. The measurement system may for example comprise a pump for generating a flow through a measurement chamber of the sensor. The controller may be configured to control the pump, e.g. to adjust a flow rate. The measurement system may further comprise one or more reservoirs, e.g. to store a solution such as a solution containing detection molecules, a dissociation solution, a buffer solution and/or a measurement solution. The controller may be configured to provide the respective solution to the sensor, e.g. as described above for the inventive method. The measurement system may further comprise a temperature sensor and/or a heating element, e.g. to control a temperature of the sensor.

LIST OF FIGURES

Figure 1B:
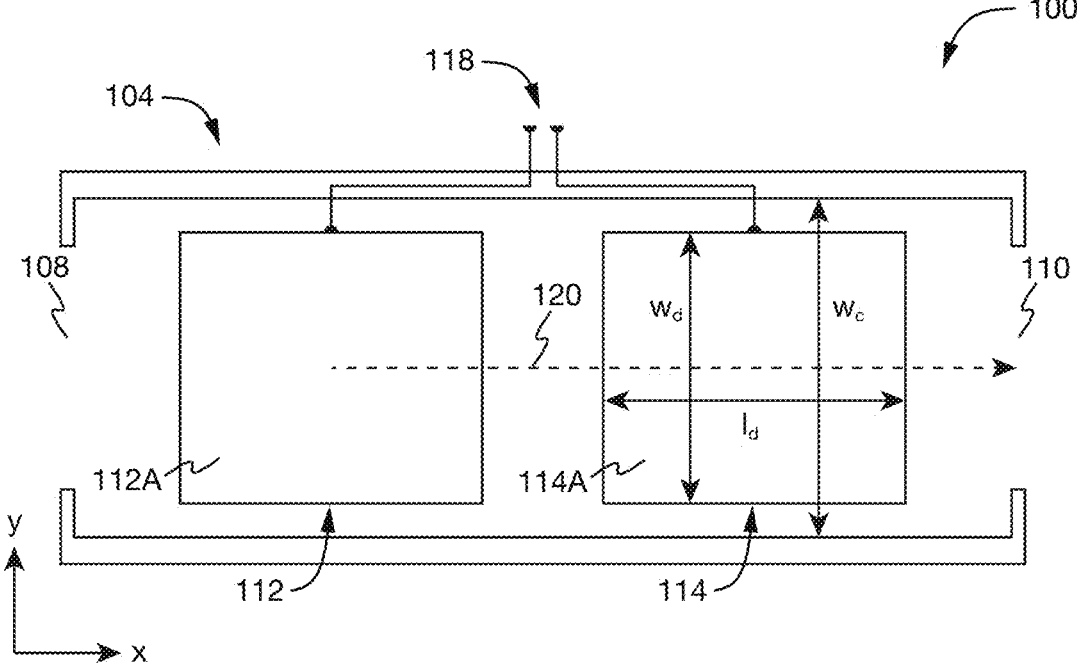
Figures 2A, 2B, 2C:
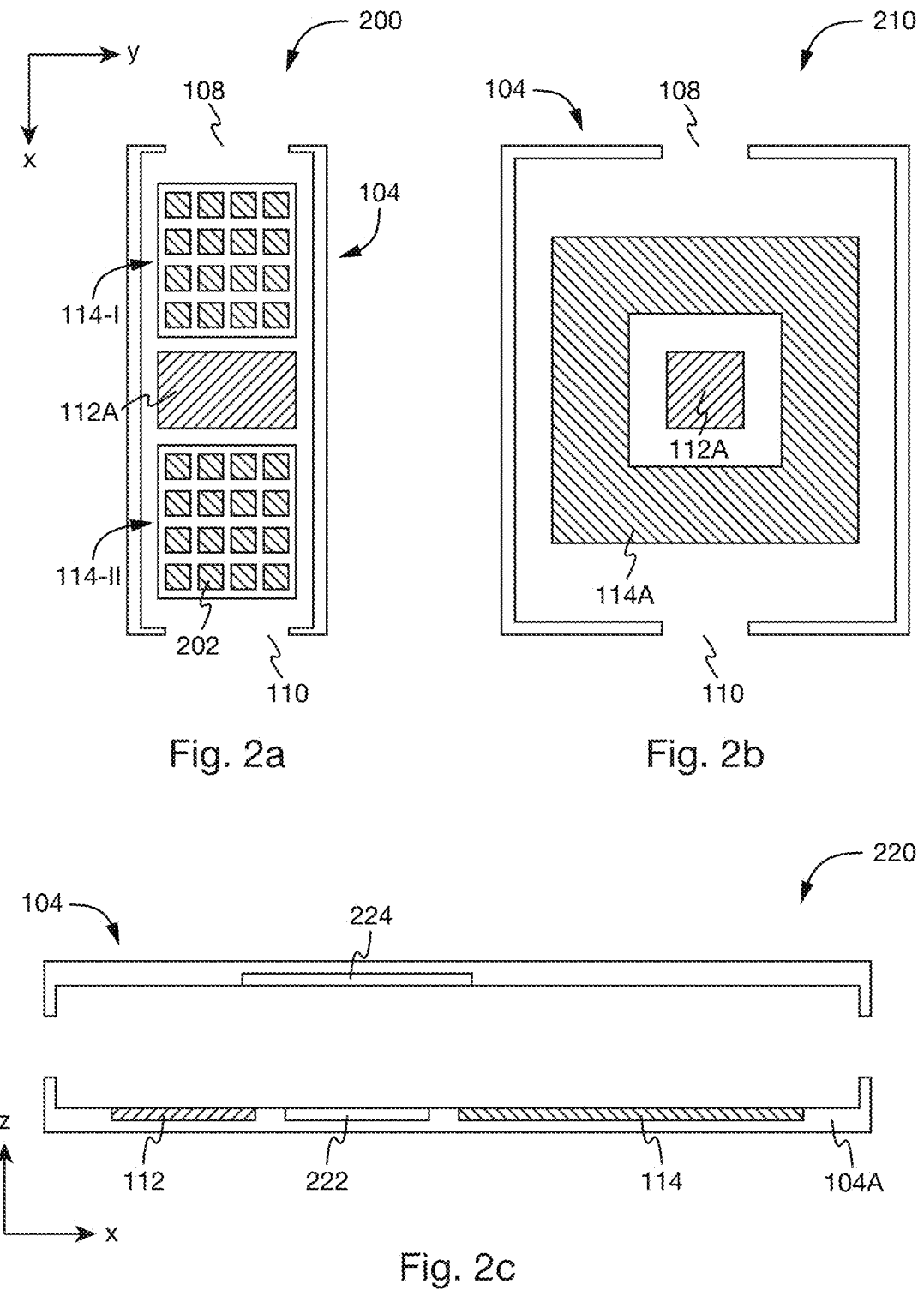
Figure 3:
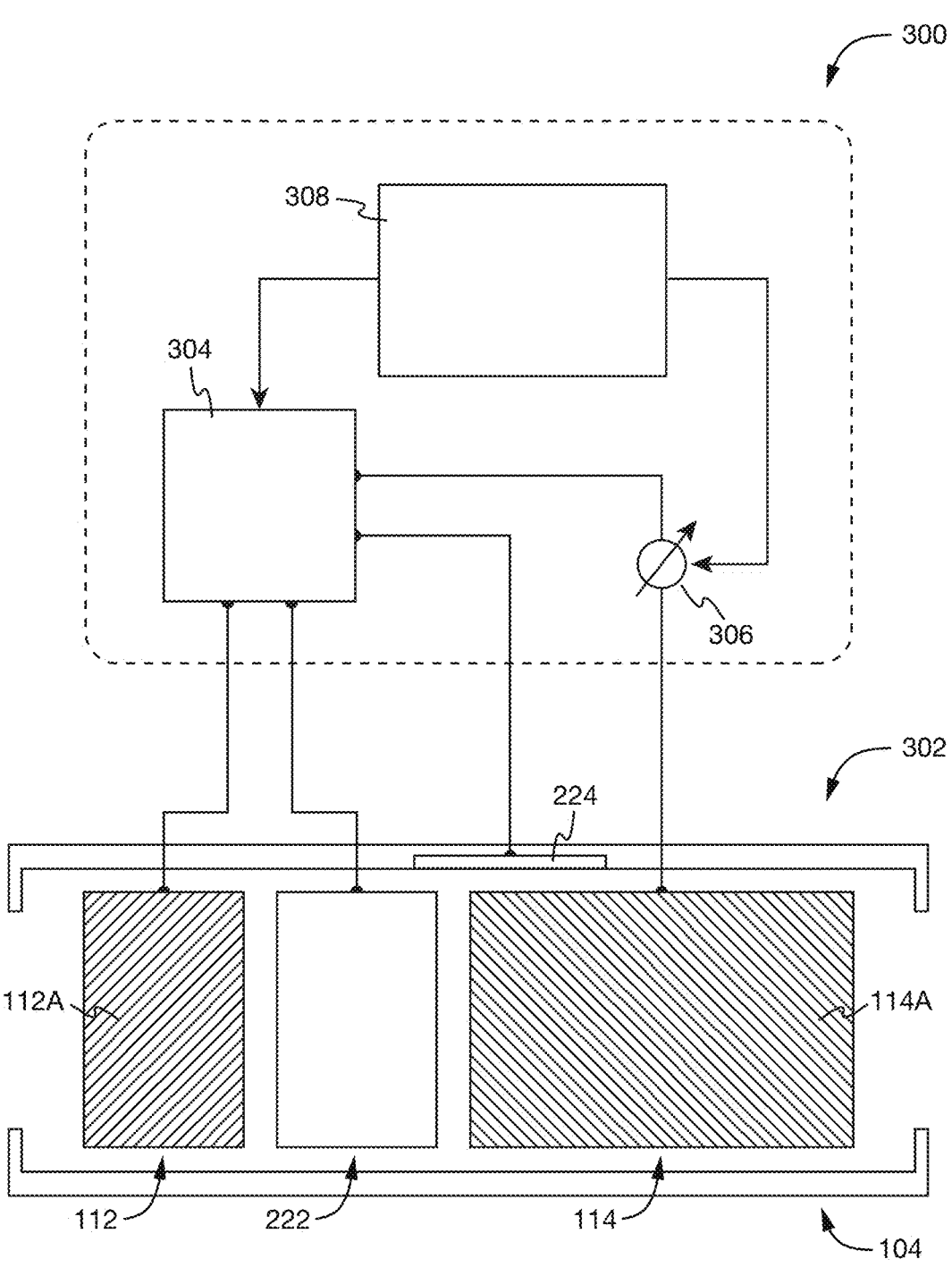
Figure 4:
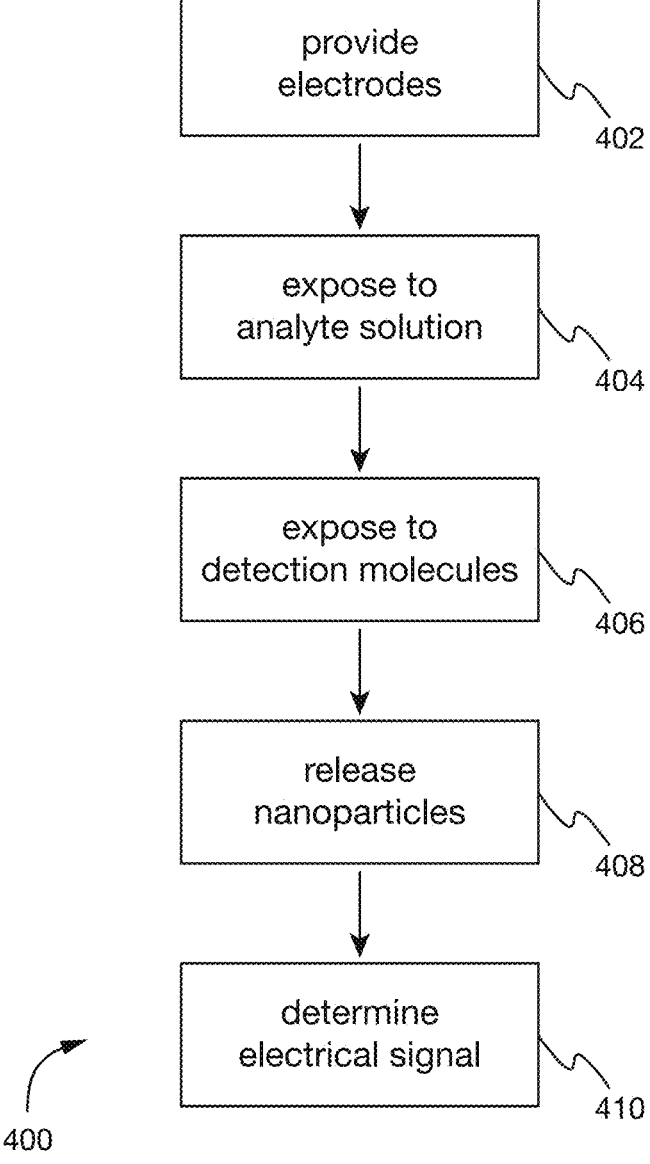
Figure 5A:
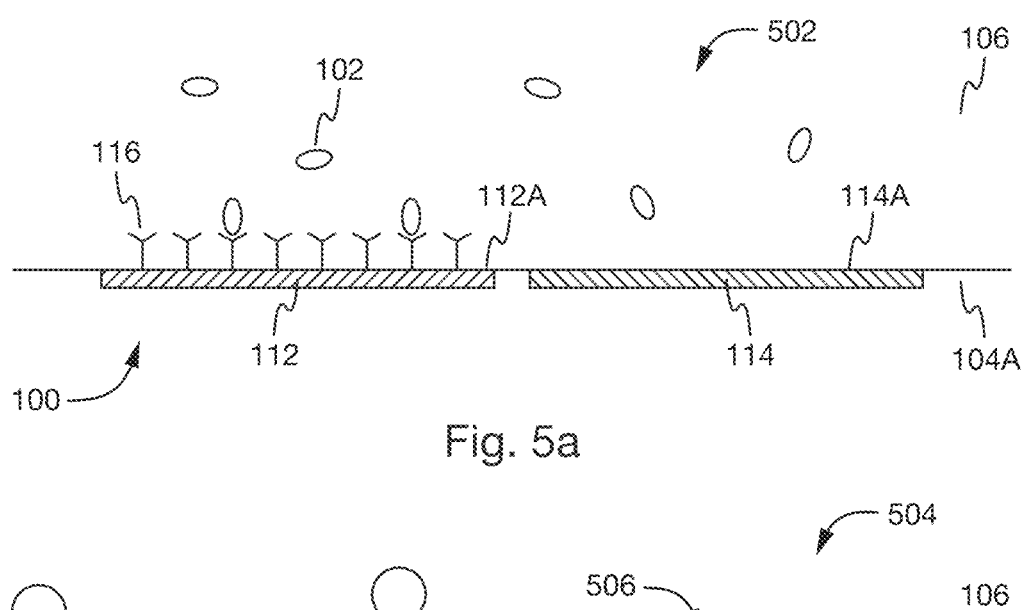
Figure 5B:
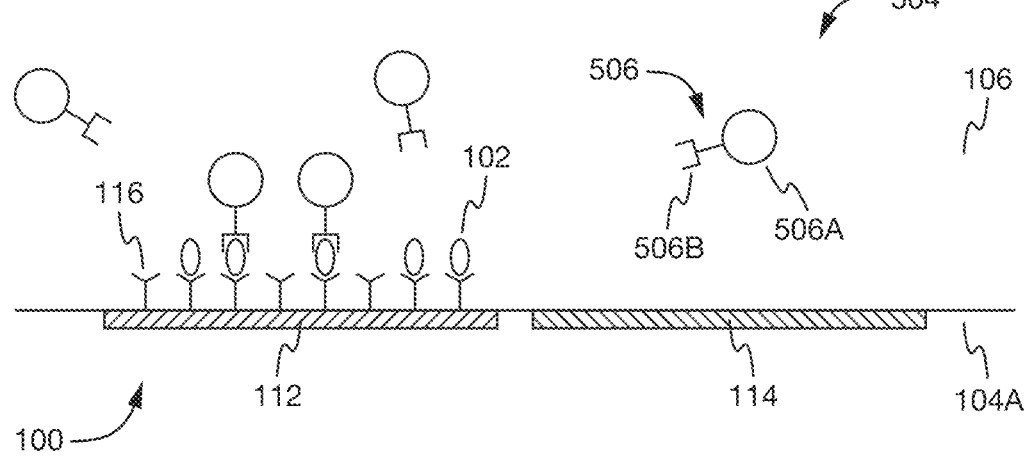
Figure 5C:
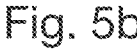
Figure 5C:
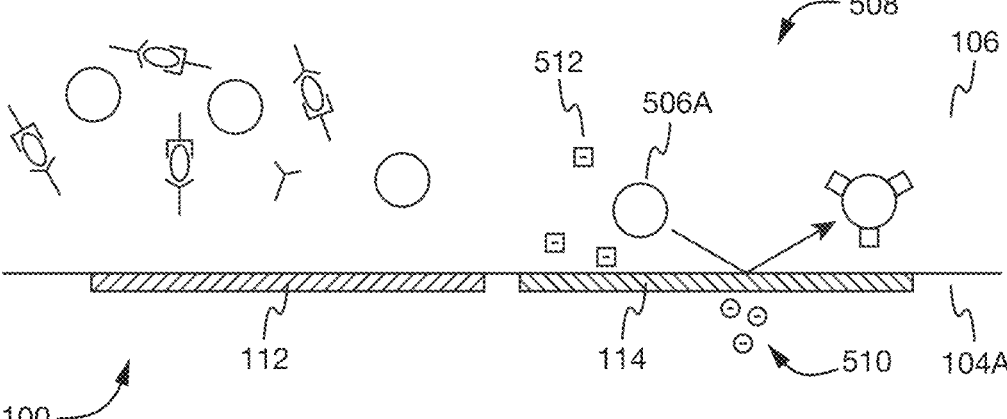
Figure 6A:
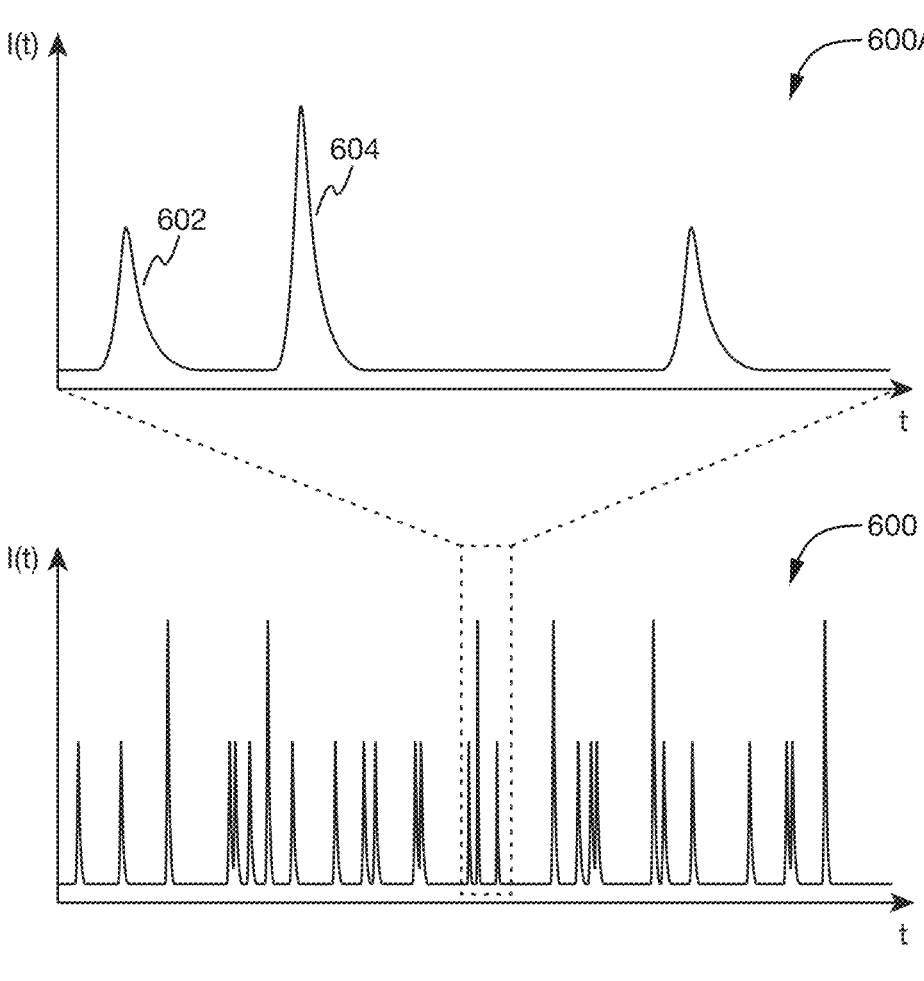
Figure 6B:
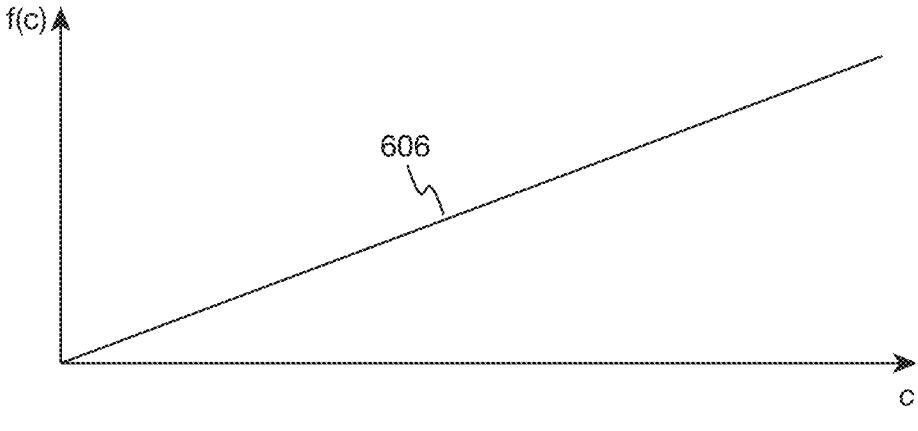

In the following, a detailed description of the invention and exemplary embodiments thereof is given with reference to the figures. The figures show schematic illustrations of FIG. 1a: a cross section of a sensor according to an exemplary embodiment of the invention in side view;

FIG. 1b: a cross section of the sensor of FIG. 1a in top view;

FIG. 2a: a cross section of a sensor comprising arrays of microelectrodes in accordance with an embodiment of the invention in top view;

FIG. 2b: a cross section of a sensor comprising a capture electrode surrounded by a detection electrode in accordance with an embodiment of the invention in top view;

FIG. 2c: a cross section of a sensor comprising a support electrode and a reference electrode in accordance with an embodiment of the invention in side view;

FIG. 3: a measurement system according to an exemplary embodiment of the invention;

FIG. 4: a flow diagram of a method for sensing target molecules in an analyte solution in accordance with an embodiment of the invention;

FIG. 5a: the binding of target molecules to capture molecules on the capture surface in accordance with an embodiment of the invention;

FIG. 5b: the binding of detection molecules to target molecules on the capture surface in accordance with an embodiment of the invention;

FIG. 5c: the release of nanoparticles from the capture surface in accordance with an embodiment of the invention;

FIG. 6a: a measurement signal according to an exemplary embodiment of the invention;

FIG. 6b: a calibration curve for determining a concentration of target molecules in accordance with an embodiment of the invention; and FIG. 7a-7d: experimental data for the sensing of target molecules through the detection of nanoparticles using a sensor in accordance with an exemplary embodiment of the invention.

DESCRIPTION OF THE PREFERRED EMBODIMENTS

FIGS. 1a and 1b depict schematic illustrations of a sensor 100 for sensing target molecules 102 in an analyte solution according to an exemplary embodiment of the invention. FIG. 1a shows a cross section of the sensor 100 in side view (not to scale) and FIG. 1b shows a cross section of the sensor 100 in top view (not to scale).

The sensor 100 comprises a measurement chamber 104 that encloses an inner volume 106. The measurement chamber 104 may e.g. be a microfluidic chamber and is thus also referred to as the microfluidic chamber 104 in the following. The microfluidic chamber 104 has an inlet 108 and an outlet 110 in fluid communication with the inner volume 106. The microfluidic chamber 104 comprises or consists of an insulating material, e.g. a glass or a polymer material. The inner volume 106 may e.g. have a volume between 0.001 mm³ and 10 mm³. In some embodiments, the microfluidic chamber 104 may be a microfluidic channel that is part of a microfluidic structure (not shown), which may comprise additional elements such as a reservoir, a pump, a valve, and/or connectors for providing and extracting the analyte solution.

The sensor 100 also comprises a capture surface 112A that is exposed to the inner volume 106, i.e. such that the capture surface 112A comes in contact with a fluid (not shown) filling the inner volume 106. The sensor further comprises a detection electrode 114 with a detection surface 114A that is also exposed to the inner volume 106. In the example of FIGS. 1a, 1b, the capture surface 112A is a surface of a capture electrode 112 separate from the detection electrode 114. The capture electrode 112 and the detection electrode 114 are embedded in a bottom wall 104A of the microfluidic chamber 104. In other examples, one or both of the electrodes 112, 114 may be arranged on the bottom wall 104A and/or may be arranged on or embedded in a different wall of the microfluidic chamber 104, e.g. a side wall or a top wall. In some examples, the capture surface 112A may not be a surface of an electrode, but may e.g. be an electrically insulated surface, for example a part of a wall of the microfluidic chamber 104. In yet another example, the detection surface 114A may also be or comprise the capture surface 112A and the sensor 100 may e.g. only comprise a single electrode 114.

The electrodes 112, 114 comprise or consist of a conducting material, in particular a metal, a metal alloy, a conducting carbon material such as graphite or glassy carbon and/or a conducting polymer material such as poly(3,4-ethylenedi-oxythiophene) polystyrene sulfonate (PEDOT:PSS). In one example, the capture surface 112A comprises or consists of gold and the detection surface 114A comprises or consists of platinum. One or both of the electrodes 112, 114 may comprise additional layers underneath the respective surface 112A, 114A, for example a substrate (not shown), which may e.g. comprise or consist of glass, polyethylene terephthalate (PET), polyethylene naphthalate (PEN), polyimide, and/or an adhesion layer (not shown), which may e.g. comprise or consist of titanium and/or chromium.

On the capture surface 112A, a plurality of capture molecules 116 is arranged, which are configured to bind to at least one of the target molecules 102 that are to be detected with the sensor 100. Each of the capture molecules 116 comprises a first functional group forming a chemical bond with the capture surface 112A. The first functional group may for example comprise sulfur, which can e.g. bind to gold atoms on the capture surface 112A. Each of the capture molecules 116 further comprises a second functional group that is configured to form a chemical bond with one of the target molecules 102. The first and second functional groups may e.g. be connected by a linker element. Each of the capture molecules 116 may in particular comprise an aptamer, an antibody or a part thereof configured to bind to one of the target molecules 102, which may e.g. be a protein comprising a corresponding antigen. In one example, each of the capture molecules 116 comprises an immunoglobulin G (IgG) or a part thereof, i.e. may be derived from an IgG as detailed below.

The capture surface 112A and/or other surfaces exposed to the inner volume 106 may comprise an anti-adsorption coating (not shown) thereon to prevent direct adsorption of target molecules 102 and/or of other molecules such as detection molecules, i.e. adsorption by means other than binding to one of the capture molecules 116. The anti-adsorption coating may e.g. be a self-assembled monolayer on the respective surface and may for example comprise or consist of polyethylene glycol, perfluorinated silanes or perfluorinated polymers.

The sensor 100 also comprises an electrical connector 118 that is configured to provide independent electrical connections to the capture electrode 112 and to the detection electrode 114, i.e. such that an electrical signal such as a current or voltage may be applied and/or measured independently at each of the electrodes 112, 114. In the example of FIG. 1b, the electrical connector 118 has two pins, each of which is electrically coupled to one of the electrode 112, 114 by a respective wire. The electrical connector 118 is configured to receive a plug for connecting a cable to the sensor 100.

In the example of FIGS. 1a, 1b, the detection electrode 114 is arranged downstream of the capture electrode 112 with regard to a flow through the microfluidic chamber 104 from the inlet 108 to the outlet 110. Accordingly, a flow path 120 along which a fluid flows from the center of the capture surface 112A to the outlet 110 when generating a flow from the inlet 108 to the outlet 110 passes over the electrode 114. Thereby, particles may be transported from the capture electrode 112 towards the detection electrode 114 by advection. The flow path 120 may also be referred to as the release flow path 120 in the following.

The microfluidic chamber 104 has an inner height $h_c$ perpendicular to the detection surface 114A, wherein the inner height $h_c$ is defined as the height of the inner volume 106 between opposing inner surfaces of the bottom wall 104A and of the opposing top wall of the microfluidic chamber 104. The height $h_c$ is less than 30%, in some examples less than 20% of a length $l_d$ of the detection surface 114A along the release flow path 120 (schematic illustrations of FIGS. 1a, 1b are not to scale). Reducing the height $h_c$ compared to the length $l_d$ may increase a probability of particles diffusing in the inner volume 106 to come in contact with the detection surface 114A.

The height $h_c$ may be adapted to diffusion properties of nanoparticles used in a method for sensing the target particles 102 according to the invention (see below), e.g. based on a radius of the nanoparticles and/or a viscosity of a solution provided to the inner volume 106. The height $h_c$ may e.g. be chosen to be a fraction of the square root of the mean square displacement of the nanoparticles during a predetermined time, e.g. a measurement duration, which may for example be between 10 s and 300 s. The height $h_c$ may for example be less than 100 μm, in some examples less than 30 μm, in one example less than 10 μm. The length $l_d$ of the detection surface 114A may for example be between 50 μm and 1000 μm, e.g. 100 μm.

A width $w_d$ of the detection surface 114A perpendicular to the release flow path 120 is at least 75%, preferably at least 90% of an inner width $w_c$ of the microfluidic chamber 104 perpendicular to the release flow path 120. The inner width $w_c$ is defined as the width of the inner volume 106 between opposing inner surfaces of the side walls of the microfluidic chamber 104. The detection surface 114A may in particular extend over the entire inner width $w_c$ of the microfluidic chamber 104. The width $w_c$ may for example be between 50 μm and 1000 μm, e.g. 100 μm.

Examples of sensors with different electrode configurations according to exemplary embodiments of the invention are depicted in FIGS. 2a, 2b, and 2c. FIGS. 2a and 2b show schematic illustrations of a sensor 200 and 210, respectively, in a cross-sectional top view (not to scale) and FIG. 2c shows a schematic illustration of a sensor 220 in a cross-sectional side view (not to scale).

The sensor 200 of FIG. 2a comprises two detection electrodes 114-I and 114-II, which are arranged on opposing sides of the capture electrode 112, i.e. such that the capture electrode 112 is sandwiched between the detection electrodes 114-I, 114-II. In this way, the probability of interacting with one of the detection electrodes 114-I, 114-II may be increased for nanoparticles released from the capture electrode 112.

Each of the detection electrodes 114-I, 114-II consists of a microelectrode array, in which a plurality of microelectrodes 202 are arranged in a regular pattern. Each of the microelectrodes 202 may for example have a surface area between 20 μm² and 200 μm². Preferably, the microelectrodes 202 cover a surface area of more than 75%, in one example more than 90% of the surface area of the respective detection electrode. Accordingly, a distance between opposing edges of adjacent microelectrodes may be less than 5 μm, in some examples less than 2 μm. Each of the detection electrodes 114-I, 114-II may for example comprise between 2 and 100 microelectrodes. The electrical connector (not shown) or a corresponding connection assembly of the sensor 200 is configured to provide individual electrical connections to each of the microelectrodes 202. Using an array of microelectrodes 202 instead of a continuous electrode 114 as in FIG. 1b may be advantageous since the microelectrodes 202 have a smaller interfacial impedance, which will reduce the noise of a current measurement using the microelectrodes 202.

The sensor 210 of FIG. 2b comprises a detection electrode 114, which encloses a capture surface 112A, e.g. a surface of a capture electrode 112, arranged in the center of the detection electrode 114. In the example of FIG. 2b, the detection electrode 114 has a rectangular circumference and encloses a rectangular cutout, in which the capture electrode 112 is arranged. In other examples, the detection electrode 114 may have a different shape, e.g. an annular shape. The inner height of the microfluidic chamber 104 perpendicular to the detection surface 114A is less than 30%, preferably less than 20% of a width of the detection surface 114A perpendicular to its circumference, i.e. the length between respective inner and outer edges of the detection surface 114A. Similar to the sensor 200, the detection electrode 114 may also consist of an array of microelectrodes (not shown). In some examples, the detection electrode 114 may only partially enclose the capture electrode 112 and may e.g. have one or more cutouts (not shown) extending outwards from the capture electrode 112.

In some examples, the detection surface 114A may comprise the capture surface 112A. The detection surface 114A may e.g. also cover the rectangular cutout, i.e. the detection surface 114A may extend over the entire rectangular area enclosed by the outer edge of the detection surface 11A in FIG. 2b (not shown). The capture surface 112A may e.g. correspond to a center portion of the detection surface 114A, i.e. the capture molecules 116 may only be arranged in the center portion. The center portion may e.g. have a similar shape as the capture surface 112A shown in FIG. 2b. In this example, the inner height of the microfluidic chamber 104 perpendicular to the detection surface 114A is less than 30%, preferably less than 20% of a length of the detection surface 114A measured from the center of the capture surface 112A to the edge of the detection surface 114A that is closest to the outlet 108. In some embodiments, the inner height of the microfluidic chamber 104 perpendicular to the detection surface 114A may be less than 30%, preferably less than 20% of a length of the detection surface 114A measured from the edge of the capture surface 112A that is closest to the outlet 108 to the edge of the detection surface 114A that is closest to the outlet 108.

FIG. 2c depicts a sensor 220, which in addition to a capture electrode 112 and a detection electrode 114 comprises a support electrode 222 and a reference electrode 224. The support electrode 222 and the reference electrode 224 are exposed to the inner volume 106 of the microfluidic chamber 104. The sensor 220 further comprises an electrical connector (not shown) that is configured to provide independent electrical connections to each of the electrodes 112, 114, 222, and 224.

The support electrode 222 is embedded in the bottom wall 104A between the capture electrode 112 and the detection electrode 114. The support electrode 222 may be similar to the capture electrode 112 and may for example be used as a second capture electrode by providing capture molecules (not shown) thereon. This may allow for sensing different types of target molecules using the sensor 220, e.g. target molecules of a first kind and target molecules of a second kind different from the first kind. The capture molecules on the capture electrode 112 may for example be configured to bind to at least one of the target molecules of the first kind, but not to target molecules of the second kind. The capture molecules on the support electrode 222, on the other hand, may for example be configured to bind to at least one of the target molecules of the second kind, but not to target molecules of the first kind.

In other examples, the support electrode 222 may be used as a guard electrode and no capture molecules may be arranged thereon. The guard electrode 222 may for example facilitate the separation of nanoparticles from remaining parts of detection molecules after release from the capture electrode 112 as detailed below.

The reference electrode 224 is embedded in a top wall of the microfluidic chamber 104 opposing the bottom wall 104A. The reference electrode may for example be used as a reference point for applying a voltage to one of the electrodes 112, 114, and 222, i.e. a potential difference may be applied between the reference electrode 224 and the respective one of the electrodes 112, 114, and 222. Preferably, the reference electrode 224 consists of a material with a stable electrochemical electrode potential. The reference electrode 224 may for example be a silver silver/chloride electrode (Ag/AgCl).

FIG. 3 depicts a schematic illustration of a measurement system 300 for sensing target molecules in an analyte solution according to an exemplary embodiment of the invention. The measurement system 300 is configured for use with a sensor comprising a capture surface and a detection electrode, e.g. one of the sensors 100, 200, 210, and 220. The sensor may be provided as an independent unit to be connected to the measurement system 300. In other examples, the sensor may be provided as part of the measurement system 300.

In the following, the measurement system 300 is described using a sensor 302 as an example. The sensor 302 is schematically illustrated in a cross-sectional top view in FIG. 3. The sensor 302 is similar to the sensor 220 and also comprises a capture electrode 112, a detection electrode 114, a support electrode 222, and a reference electrode 224. The capture electrode 112, the detection electrode 114, and the support electrode 222 are arranged on or embedded in a bottom wall of a microfluidic chamber 104, whereas the reference electrode 224 is embedded in a side wall of the microfluidic chamber 104. The measurement system 300 may for example be configured to be connected to an electrical connector (not shown) of the sensor 302 through a cable or may comprises a mount (not shown) for attaching the sensor 302. This may allow for exchanging the sensor 302 easily.

The measurement system 300 comprises a voltage source 304, an ammeter 306, and a controller 308, which may be integrated into a single device or may be independent units. The voltage source 304 is configured to apply a voltage to the capture electrode 112. The voltage source 304 is further configured to apply a voltage to each of the electrodes 114, 222, and 224 independently, i.e. the voltage source 304 comprises four independent outputs. The voltage source 304 may for example be configured to apply a voltage to each of the electrodes 112, 114, and 222 relative to the reference electrode 224 within a range between −2V and +2V. In the following, "applying a voltage to an electrode" is thus to be understood as applying the respective voltage between the electrode and the reference electrode 224. In some examples, the measurement system 300 may not comprise the voltage source 304, but may instead be configured to be connected to an external voltage source (not shown) that provides the respective functionality and is controlled by the controller 308 as described below.

The ammeter 306 is configured to measure a current through the detection electrode 114, e.g. within a range between −100 nA and 100 nA with a limit of detection of at least 10 pA, preferably at least 1 pA, and a sampling rate of at least 500 Hz, preferably at least 10 kHz. The ammeter 306 may comprise an amplifier for amplifying the current to be measured. The ammeter 306 can comprise a plurality of independent channels (not shown), e.g. for the measurement of currents through individual microelectrodes.

The controller 308 may be implemented in hardware, software, or a combination thereof. The controller 308 may in particular comprise a microcontroller (not shown) with a processor and a storage medium containing instructions to be executed by the processor to provide the functionality described in the following. The controller 308 is configured to execute at least a part of the method 400 described below, in particular steps 408 and 410. The controller 308 is configured to control the voltage source 304, e.g. by providing analog or digital control signals. The controller 308 is further configured to control the ammeter 306, e.g. by providing analog or digital trigger signals for initiating and terminating a measurement and/or by reading out one or more analog or digital measurement signals from the ammeter 306.

The controller 308 is configured to initiate a dissociation process to release electrochemically active nanoparticles adsorbed on the capture surface 112A. In particular, the controller 308 is configured to apply a disassociation voltage to the capture electrode 112 via the voltage source 304 to release electrochemically active nanoparticles adsorbed on the capture electrode 112 by electrically and/or electrochemically induced dissociation, e.g. as detailed below. The controller 308 is further configured to apply a bias voltage to the detection electrode 114 via the voltage source 304, e.g. while measuring a current through the detection electrode 114 via the ammeter 306 (see below). The controller 308 is also configured to apply a dissociation voltage to the support electrode 222 via the voltage source 304, e.g. to release electrochemically active nanoparticles adsorbed on the support electrode 222 by electrically and/or electrochemically induced dissociation or to separate nanoparticles from remaining parts of detection molecules by electrically and/or electrochemically induced dissociation (see below).

The controller 308 is configured to determine a measurement signal characterizing the current through the detection electrode 114 as a function of time using the ammeter 306. The measurement signal may characterize the total current through the detection electrode 114 or may characterize the currents through each of a plurality of microelectrodes (not shown) making up the detection electrode 114.

The controller 308 is further configured to determine a number of impact events from the measurement signal, wherein the impact events are caused by an electrochemical reaction during impact of a nanoparticle on the detection electrode as detailed below. For this, the controller 308 is configured to identify spikes in the measurement signal (see below). The controller 308 may further be configured to obtain a parameter of an impact event such as a current amplitude and/or a time-integrated current associated with an impact event from the measurement signal (see below). The controller 308 may also be configured to extract a parameter associated with the respective nanoparticle from the measurement signal and/or parameters of the impact event, e.g. a size of the nanoparticle as described below.

FIG. 4 shows a flowchart of a method 400 for sensing target molecules 102 in an analyte solution according to an exemplary embodiment of the invention. The method 400 may for example be executed with a sensor and a measurement system according to the invention and is described in the following using the measurement system 300 and the sensor 100 as an example. Some of the steps of the method 400 are illustrated in FIGS. 5a to 5c.

The method 400 comprises, in step 402, providing the capture surface 112A and the detection electrode 114, e.g. by providing the sensor 100 with the capture electrode 112 and the detection electrode 114. The sensor 100 is provided as a functionalized sensor, wherein a plurality of capture molecules 116 are already arranged on the capture surface 112A, each of which is configured to bind to at least one of said target molecules 102.

In other examples, the sensor 100 may be provided as a bare sensor without capture molecules 116 on the capture surface 112A and step 402 may comprise adsorbing capture molecules 116 on the capture surface 112A, e.g. by chemisorption. For this, the capture surface 112A may be exposed to a solution containing the capture molecules 116 or a precursor thereof. Each of the capture molecules 116 may e.g. comprise a first functional group that is configured to form a chemical bond with the capture surface 112A. The capture surface 112A may e.g. consist of gold and the first functional group may be a sulfur group such as a thiol or a disulfide, which is configured to bind to the gold surface. Such capture molecules may for example be derived from an immunoglobulin G (IgG), e.g. by dissociating an IgG tetramer into its two identical halfs, each of which comprises an antigen binding site as a second functional group. The two fragments may be reduced using a reducing agent such as 2-mercaptoethylamine to create free sulfhydryl groups. Subsequently, the capture surface 112A may be exposed to a solution containing the reduced fragments to allow for chemisorption of the reduced fragments on the capture surface 112A. The incubation time during which the capture surface 112A is exposed to the capture molecule solution may be adjusted to the reaction kinetics of the binding reaction between the capture molecules 116 and the capture surface 112A, the concentration of capture molecules 116 in the solution and/or the size of the capture surface 112A. Thereby, a density of capture molecules 116 on the capture surface 112 may be achieved which is appropriate for an expected concentration of target molecules in the analyte solution to be probed, i.e. provides sufficient sensitivity and measurement range to allow for a determination of the concentration of target molecules. Step 402 may further comprise coating the capture surface 112A with an anti-adsorption coating, e.g. to prevent direct adsorption of target molecules 102 and/or of other molecules such as detection molecules.

The method 400 further comprises, in step 404, exposing the capture surface 112A to the analyte solution 502 that is to be probed as illustrated in FIG. 5a, e.g. by filling the inner volume 106 of the microfluidic chamber 104 with the analyte solution 502. Thereby, target molecules 102 contained in the analyte solution 502 can bind to the capture molecules 116 arranged on the capture surface 112A. As described above with reference to FIGS. 1a, 1b, each of the capture molecules 116 comprises at least one second functional group that is configured to form a chemical bond with one of the target molecules 102, e.g. a matching antigen binding site for a protein to be detected such as e.g. insulin.

The incubation time during which the capture surface 112A is exposed to the analyte solution 502 may be adjusted to the reaction kinetics of the binding reaction between the capture molecules 116 and the target molecules 102, the concentration of capture molecules 116 on the capture surface 112A, the expected concentration of target molecules 102 in the analyte solution 502, and/or diffusion properties of the target molecules 102 in the analyte solution 502. The incubation time may e.g. be chosen to be sufficiently large to establish an equilibrium between the capture molecules 116 on the capture surface 112A and the analyte solution 502, i.e. such that the number of target molecules bound to the capture molecules 116 is approximately constant. In some examples, the incubation time may be chosen such that a certain fraction of target molecules 102 from the analyte solution 502, e.g. a fraction between 50% and 100%, is adsorbed by the capture molecules 116. The incubation time may for example be between 5 s and 300 s. Preferably, the number of capture molecules 116 on the capture surface 112A and/or the expected concentration of target molecules 102 in the analyte solution 502 is chosen such that the capture molecules 116 on the capture surface 112A are not saturated, i.e. free binding sites remain at the end of the incubation time, e.g. by diluting the analyte solution 502 accordingly. Step 404 may also comprise generating a flow of the analyte solution 502 in the inner volume 104, e.g. to direct target molecule 102 towards the capture surface 112A by advection and/or to generate a thin diffusion layer above the capture surface 112A by advection. This may allow for a smaller incubation time to achieve a given adsorption rate of target molecules 102.

The method 400 further comprises, in step 406, exposing the capture surface 112A to a solution 504 containing detection molecules 506 as illustrated in FIG. 5b. Each of the detection molecules 506 contains an electrochemically active nanoparticle 506A. In the context of this disclosure, the term "electrochemically active nanoparticle" refers to a nanoparticle that is configured to undergo a chemical reaction with one or more other substances, wherein the chemical reaction involves the release or absorption of one or more free charged particles, in particular free electrons, e.g. to/from the detection electrode 114 as detailed below. The reaction partner may e.g. be an ion in an electrolyte solution and/or may be the detection surface 114A itself.

The nanoparticles 506A may in particular be metal nanoparticles, which consist of or comprise metal, e.g. one or more metals selected from the group consisting of silver, copper, gold and platinum. Preferably, a surface of the nanoparticles 506A consists of a different material than the detection surface 114A and/or the capture surface 112A. In one example, a detection electrode 114 consisting of platinum is used for nanoparticles 506A comprising silver. In another example, a detection electrode 114 consisting of a conducting carbon material such as graphite or glassy carbon is used for nanoparticles 506A comprising gold or platinum. The nanoparticles 506A may e.g. have a spherical or ellipsoidal shape and may have a diameter between 5 nm and 100 nm, e.g. 20 nm. Nanoparticles of this size may e.g. have a surface area that is sufficiently large to release/absorb a charge through electrochemical reactions during impact on the detection electrode that is large enough to be detected by an ammeter connected to the detection electrode 114 such as the ammeter 308. On the other hand, nanoparticles of this size may be sufficiently small such that an impact on the detection electrode 114 may generate a well-defined current spike as described in more detail below.

Each of the detection molecules 506 is further configured to bind to one of the target molecules 102 that are bound to a capture molecule 116 on the capture surface 112A. For this, each of the detection molecules 506 comprises a functional group 506B configured to bind to a binding site on the target molecules 102 that is different from a binding site on the target molecules 102 to which the capture molecules 116 bind. Each of the detection molecules 506 may in particular comprise an aptamer, an antibody or a part thereof configured to bind to one of the target molecules 102. By exposing the capture surface 112A to the solution 504, the electrochemically active nanoparticles 506A can thus bind to the capture surface 112A through the formation of "sandwich" structures with one of the target molecules 102 and one of the capture molecules 116 bound to the capture surface 112A, similar to enzyme-linked immunosorbent assays (ELISAs).

The incubation time during which the capture surface 112A is exposed to the solution 504 may be adjusted to the reaction kinetics of the binding reaction between the detection molecules 506 and the target molecules 102, the expected concentration of target molecules 102 on the capture surface 112A, the concentration of detection molecules 506 in the solution 504, and/or diffusion properties of the detection molecules 506 in the solution 504. The incubation time may e.g. be chosen to be sufficiently large to establish an equilibrium between the target molecules 102 immobilized on the capture surface 112A and the solution 504, i.e. such that the number of detection molecules 506 bound to the capture surface 112A is approximately constant. The incubation time may for example be between 5 s and 300 s. Preferably, the number of detection molecules 506 in the solution 504 is chosen to be much larger than the number of target molecules 102 and/or capture molecules 116 on the capture surface 112A to completely saturate the target molecules 102. In some examples, the concentration of detection molecules 506 in the solution 504 and/or the incubation time may be chosen such that a certain fraction of target molecules 102 on the capture surface 112A, e.g. more than 90%, preferably more than 95%, bind to one of the detection molecules 506. Similar to step 404, step 406 may also comprise generating a flow of the solution 504 in the inner volume 104, e.g. to direct detection molecules 506 towards the capture surface 112A by advection and/or to generate a thin diffusion layer above the capture surface 112A by advection. This may allow for a smaller incubation time to achieve a given adsorption rate of detection molecule 506.

The method 400 further comprises, at step 408, releasing nanoparticles 506A that are bound to the capture surface 112A. For this, the solution 504 is completely removed from the inner volume 106 prior to releasing the nanoparticles 506A from the capture surface 112A and is replaced by a measurement solution 508 that does not contain any nanoparticles 506A, e.g. an electrolyte solution. Thereby, one can ensure that only nanoparticles 506A that were previously bound to one of the target molecules 102 are present in the inner volume 106 after the release. The nanoparticles 506A are released from the capture surface 112A, e.g. by applying a dissociation voltage to the capture electrode 112 to electrically and/or electrochemically dissociate the nanoparticles 506A from the capture surface 112A. The dissociation voltage is chosen to be sufficiently large to break metal-sulfur bonds between the capture surface 112A and the capture molecules 116 and/or to break bonds between the nanoparticles 506A and the remaining part of the detection molecules 506 including the functional group 506B. Preferably, at least the bonds between the nanoparticles 506A and the remaining part of the detection molecules 506 are broken to create free nanoparticles 506A. The dissociation voltage may e.g. be in the range between −2 V and 2 V and may for example be applied for a duration between 1 µs to 1 s. In some examples, the nanoparticles 506A are released from the capture surface 112A by exposing the capture surface 112A to a dissociation solution to chemically dissociate the nanoparticles 506A from the capture surface 112A. This may e.g. comprise adding a dissociating agent to the measurement solution 508.

If the sensor comprises a guard electrode, e.g. the support electrode 222 of the sensor 220, step 408 may also comprise applying a voltage to the guard electrode. If a nanoparticle 506A released from the capture surface 112A is still attached to another structure, e.g. the remaining part of the corresponding detection molecule 506 or a part thereof, the voltage at the guard electrode 222 may break the respective bond if the nanoparticle 506A and/or the other structure comes in contact with the guard electrode 222. The voltage applied to the guard electrode 222 may e.g. be similar to the dissociation voltage applied to the capture electrode 112.

In step 410, which is illustrated in FIG. 5c, an electrical signal is determined at the detection electrode 114, namely by determining, via the ammeter 306 and the controller 308, a measurement signal characterizing the current flowing through the detection electrode 114 or, preferably, the total current flowing through the plurality of microelectrodes 202 forming the detection electrode 114. A measurement solution 508 is provided prior to releasing the nanoparticles 506A and prior to determining the measurement signal. The measurement solution 508 may in particular be an electrolyte solution as detailed below. The measurement signal may e.g. be determined starting simultaneously with or shortly after releasing the nanoparticles 506A from the capture surface 112A and for a measurement duration between 1 s and 180 s. Preferably, the measurement duration is chosen such that each of the nanoparticles 506A released from the capture surface 112A has a probability larger than 95%, in some examples larger than 99% of interacting with the detection surface 114A during the measurement. This may be achieved by choosing an appropriate design for the microfluidic chamber 104 and the detection electrode 114, in particular the distances $h_c$, $l_d$, $w_d$, and $w_c$, and/or adjusting the measurement duration to the diffusion constant of the nanoparticles 506A in the electrolyte solution 508 and the geometry of the microfluidic chamber 104. Step 410 may also comprise generating a flow of the measurement solution 508 in the inner volume 104 to direct nanoparticles 506A towards the detection surface 114A by advection and/or to generate a thin diffusion layer above the detection surface 114A by advection. This may allow for increasing the probability of the nanoparticles 506A to interact with the detection surface 114A.

After the release of the nanoparticles 506A in step 408, the nanoparticles 506A can diffuse within the inner volume 106. While diffusing, a nanoparticle 506A may hit the detection surface 114A. During the impact, the nanoparticle 506A may undergo an electrochemical reaction, resulting in the release or absorption of electrons 510 to/from the detection electrode 114. This may be detected as a spike or peak in the measurement signal. An example for this is shown in FIG. 6a, in which the lower plot depicts a measurement signal 600 and the upper plot depicts a zoomed-in portion 600A of the measurement signal 600.

Impact of a nanoparticle 506A causes a transient spike 602 in the measurement signal 600. In the context of this disclosure, impact of a nanoparticle 506A on the detection electrode 114 is to be understood as the nanoparticle 506A coming close enough to the detection electrode 114 for the electrochemical reaction to take place. In some examples, this may not require direct contact between the nanoparticle 506A and the detection electrode 114 as the released/absorbed electrons may tunnel between the nanoparticle 506A and the detection electrode 114. Preferably, the electrochemical reaction during impact inactivates the respective nanoparticle, i.e. such that no reaction takes place during a subsequent impact on the detection electrode 114. The electrochemical reaction may e.g. fully oxidize the surface of the nanoparticle 506A.

Preferably, the measurement solution 508 is an electrolyte solution, which contains ions 512 that are configured to undergo a chemical reaction with one of the nanoparticles 506A during impact, wherein the chemical reaction involves the release or absorption of one or more free electrons 510 to/from the detection electrode 114. The concentration of ions 512 in the electrolyte solution may e.g. be between 1 mmol/L and 1 mol/L. In one example, the nanoparticles 506A may be silver nanoparticles and the measurement solution 508 may contain chloride ions. In the vicinity of the detection electrode 114, an oxidation reaction $$Ag + Cl^- \rightarrow AgCl + e^-$$

maytake place on the surface of the silver nanoparticles, wherein the released electrons are transferred to the detection electrode 114. To facilitate the oxidation of the silver nanoparticles, a positive bias voltage may be applied to the detection electrode 114, e.g. using the voltage source 304 and the controller 308. The bias voltage may e.g. be between +100 mV and +1 V vs. Ag/AgCl. The oxidation of the surface inactivates the silver nanoparticle such that no charge is transferred during a subsequent impact on the detection electrode 114.

The method 400 may further comprise determining a concentration of target molecules 102 in the analyte solution 502 from the measurement signal, e.g. using the controller 308. In some examples, the controller 308 may determine the concentration by determining an average current from the measurement signal 600 as the average current scales with the number of impacts of nanoparticles 506A on the detection electrode 114 and thus the number of target molecules 102 on the capture surface 112A. For this, the controller 508 may use a pre-determined calibration curve associating a given average current to a concentration of target molecules 102.

Preferably, the controller 308 determines the concentration of target molecules 102 in the analyte solution 502 by determining an impact frequency of nanoparticles 506A hitting the detection electrode 114. For this, the controller 308 detects impact events in the measurement signal 600, which are associated with the impact of one of the nanoparticles 506A on the detection electrode 114. The controller 308 is in particular configured to identify spikes such as the spike 602 in the measurement signal 600 to determine the number of impact events. The controller 308 may for example identify a spike by comparing the measurement signal with a lower and/or upper threshold value. The controller 308 may further determine a duration, a time-integrated amplitude and/or a shape of the identified spike, e.g. to confirm that the identified spike is compatible with an impact of a nanoparticle 506A. This may also comprise fitting a pre-defined fit function to the measurement signal 600, which may e.g. allow for correctly identifying partially overlapping spikes. The controller 308 is configured to determine the concentration of target molecules 102 in the analyte solution 502 using a pre-determined calibration curve such as the calibration curve 606 of FIG. 6b, which associates a frequency f of impact events with a corresponding concentration c of target molecules 102.

The method 400 may be modified in a variety of ways, some of which are discussed in the following. The method 400 may for example also comprise a step of rinsing the capture surface 112A and/or the detection electrode 114 with a buffer solution, e.g. by creating a flow of the buffer solution from the inlet 108 to the outlet 110. The buffer solution may for example contain sodium chloride and phosphate buffer. The rinsing may for example be conducted between steps 406 and 408, i.e. after exposing the capture surface 112A to the solution containing the detection molecules 116 and prior to releasing the nanoparticles 506A from the capture surface 112A. This may for example be advantageous to reduce non-specific adsorption of nanoparticles 506A, e.g. on the capture surface 112A and/or the detection electrode 114. In some examples, only the detection electrode 114 may be rinsed, e.g. by removing the detection electrode 114 from the sensor 100 or by dividing the inner volume 106 into two isolated parts, which are not in fluid communication with one another.

The method 400 may further be modified for sensing target molecules of two or more different kinds, e.g. target molecules of a first kind and target molecules of a second kind such as two different types of proteins. For this, a sensor with two or more capture surfaces, for example two or more capture electrodes, is provided in step 402, e.g. the sensor 220 using the support electrode 222 as a second capture electrode. Capture molecules of different kinds are arranged on the different capture surfaces, e.g. capture molecules of a first kind on the capture electrode 112 and capture molecules of a second kind on the support electrode 222. Capture molecules of the first kind are configured to bind to one of the target molecules of the first kind and capture molecules of second kind are configured to bind to one of the target molecules of the second kind.

Subsequently, in step 406, the capture surfaces are exposed to a solution containing detection molecules of a first kind and detection molecules of a second kind. Detection molecules of the first kind are configured to bind to one of the target molecules of the first kind bound to a capture molecule of the first kind and detection molecules of second kind are configured to bind to one of target molecules of the second kind bound to a capture molecule of the second kind. In other examples, only one kind of detection molecules may be used, wherein each of the detection molecules is configured to either bind to one of the target molecules of the first kind bound to a capture molecule of the first kind or to a target molecule of the second kind bound to a capture molecule of second kind.

Steps 408 and 410 are then executed sequentially for the capture electrode 112 and the support electrode 222, e.g. using the controller 308. In other words, at first nanoparticles are released e.g. from the capture electrode 112 and a first electrical signal is determined at the detection electrode 114 and subsequently nanoparticles are released from the support electrode 222 and a second electrical signal is determined at the detection electrode 114. After determining the first electrical signal and prior to releasing nanoparticles from the support electrode 222, the microfluidic chamber 104 is rinsed using a buffer solution to remove the nanoparticles released from the capture electrode 112. The method may further comprise determining a concentration of the target molecules of the first kind and a concentration of the target molecules of second kind, e.g. as described above.

In other examples, target molecules of two or more different kinds may be sensed using a sensor with a single capture surface, e.g. the sensor 100 with the capture electrode 112. In this case, different kinds of nanoparticles are employed which may cause distinguishable impact events such that contributions of the different kinds of nanoparticles to the electrical signal can be separated, e.g. as described in the following example. This may allow for determining a number of impact events and/or a concentration for each of the different kinds of target molecules in parallel. In step 406, detection molecules of a first kind and detection molecules of a second kind are provided, e.g. in a single solution or in two different solutions, wherein each of the detection molecules of the first kind is configured to bind to one of the target molecules of the first kind, but not to one of the target molecules of the second kind, and each of the detection molecules of the second kind is configured to bind to one of the target molecules of the second kind, but not to one of the target molecules of the first kind. Each of the detection molecules contains a nanoparticle, but the nanoparticles are different for the two kinds of detection molecules. A charge transferred to the detection electrode during impact of a nanoparticle of the first kind may be larger or smaller than a charge transferred to the detection electrode during impact of a nanoparticle of the second kind, e.g. at least 20% larger, in some examples at least 50% larger than the charge transferred to the detection electrode during impact of a nanoparticle of the second kind. The nanoparticles may for example differ in their constituents and/or their size. Each detection molecule of the first kind may e.g. contain a nanoparticle consisting of a first kind of metal and each detection molecule second kind may contain a nanoparticle consisting of a second kind of metal different from the first kind of metal. In another example, detection molecules of the first and second kinds may contain a nanoparticle of the same kind of metal, but having a different surface area and/or a different volume. A surface area of the metal nanoparticles of the first kind may for example be at least 20%, preferably at least 50% larger than a surface area of the metal nanoparticles of the second kind. This may for example result in a difference in the transferred charge when using gold nanoparticles, which tend to only or predominantly oxidize on their surface during impact. Additionally or alternatively, a volume of the nanoparticles of the first kind may for example be larger or smaller than a volume of the nanoparticles of the second kind, e.g. at least 20% larger, preferably at least 50% larger than the volume of the nanoparticles of the second kind. This may for example result in a difference in the transferred charge when using silver nanoparticles, which tend to oxidize on their surface as well as in their interior or core during impact. In this way, nanoparticles of the first kind may release a different number of electrons upon impact on the detection electrode 114 than nanoparticles of the second kind, causing spikes with a larger amplitude in the measurement signal.

An example of this is illustrated in FIG. 6c. In the measurement signal 600, two types of spikes occur, namely spikes such as spikes 602 with a smaller amplitude and spikes such as spikes 604 with a larger amplitude. The spikes 604 are for example associated with an impact of a metal nanoparticle of the first kind on the detection electrode 114, whereas the spikes 602 are associated with the impact of a metal nanoparticle of the second kind on the detection electrode 114. Impact events of the two types may for example be distinguished using an amplitude threshold or by determining a peak amplitude and/or a time-integrated amplitude, e.g. using the controller 308. Thereby, the number of impact events can be determined independently for each of the two kinds of nanoparticles. The method 400 may further comprise determining a concentration of the target molecules of the first kind and a concentration of the target molecules of the second kind from the two numbers of impact events, e.g. using corresponding calibration curves similar to the calibration curve 606.

FIGS. 7a-7d show experimental data for the sensing of target molecules (streptavidin) through the detection of nanoparticles using a sensor according to an exemplary embodiment of the invention, e.g. a sensor similar to the sensor 210 of FIG. 2b.

The employed sensor comprised a 2.54 mm×2.54 mm borosilicate glass substrate having a thickness of 500 μm and a detection electrode comprising an array of 62 circular platinum microelectrodes with a radius of about 4 μm each in a regular spacing of 200 μm from center to center. The platinum microelectrodes were arranged in a rectangular layout surrounded by a large rectangular capture electrode having a surface area of about 2.9 mm². A glass ring (diameter 17 mm) was glued on top of the chip to provide a reservoir or measurement chamber for the applied solutions.

A capture layer was immobilized on the electrodes via incubation of 50 μl cysteamine aqueous solution (5 mM) for 10 minutes at 37° C. to form a self-assembled cysteamine monolayer. Activation of the amine groups was performed using standard EDC/s-NHS (N-(3-Dimethylaminopropyl)-N'-ethylcarbodiimid-hydrochlorid/N-Hydroxysulfosuccinimide sodium salt). To this end, incubation was performed in 25 μl of 4 mg/ml EDC and 6 mg/ml s-NHS each in 0.05 MES buffer at pH5 and 37° C. for 30 minutes. The attachment of capture molecules (biotin) for capturing the target molecule streptavidin was performed via incubation of 50 μl of 0.25 mg/ml biotin in PBS for 60 minutes at 37° C.

The measurements were conducted using silver nanoparticles (AgNP) with an average diameter of about 15 nm. The biofunctionalized silver nanaoparticles were synthesized using standard procedures using sodium borohydride (NaBH₄), silver nitrate (AgNO₃), and cysteamine as a capping agent. The bioconjugation of the as synthesized cysteamine-silver nanoparticles was performed using EDC/s-NHS activation and incubation in aqueous biotin solution as described above.

The measurements were performed after incubation of the electrodes with 20 μl analyte solution (100 μM streptavidin in water) for 60 minutes at room temperature to allow the target molecules to bind to the capture molecules arranged on the capture surface. All subsequent detection steps were performed in 35 mM KCl, 50 mM KOH (pH14) solution.

Instead of or in addition to silver nanoparticles, other electrochemically active nanoparticles could be used, for example nanoparticles comprising or consisting of an electrochemically active metal such as gold and/or platinum, an electrochemically active oxide such as iridium oxide, and/or an electrochemically active polymer material such as poly (3,4-ethylenedioxythiophene):polystyrene sulfonate (PEDOT:PSS). In other examples, composite nanoparticles comprising a core of a material that is not electrochemically active with a coating of an electrochemically active material such as silver may be used. The core of the composite nanoparticles may for example comprise or consist of silicon dioxide, silicon nitride, and/or a non-conductive polymer material such as polystyrene.

Figure 7:
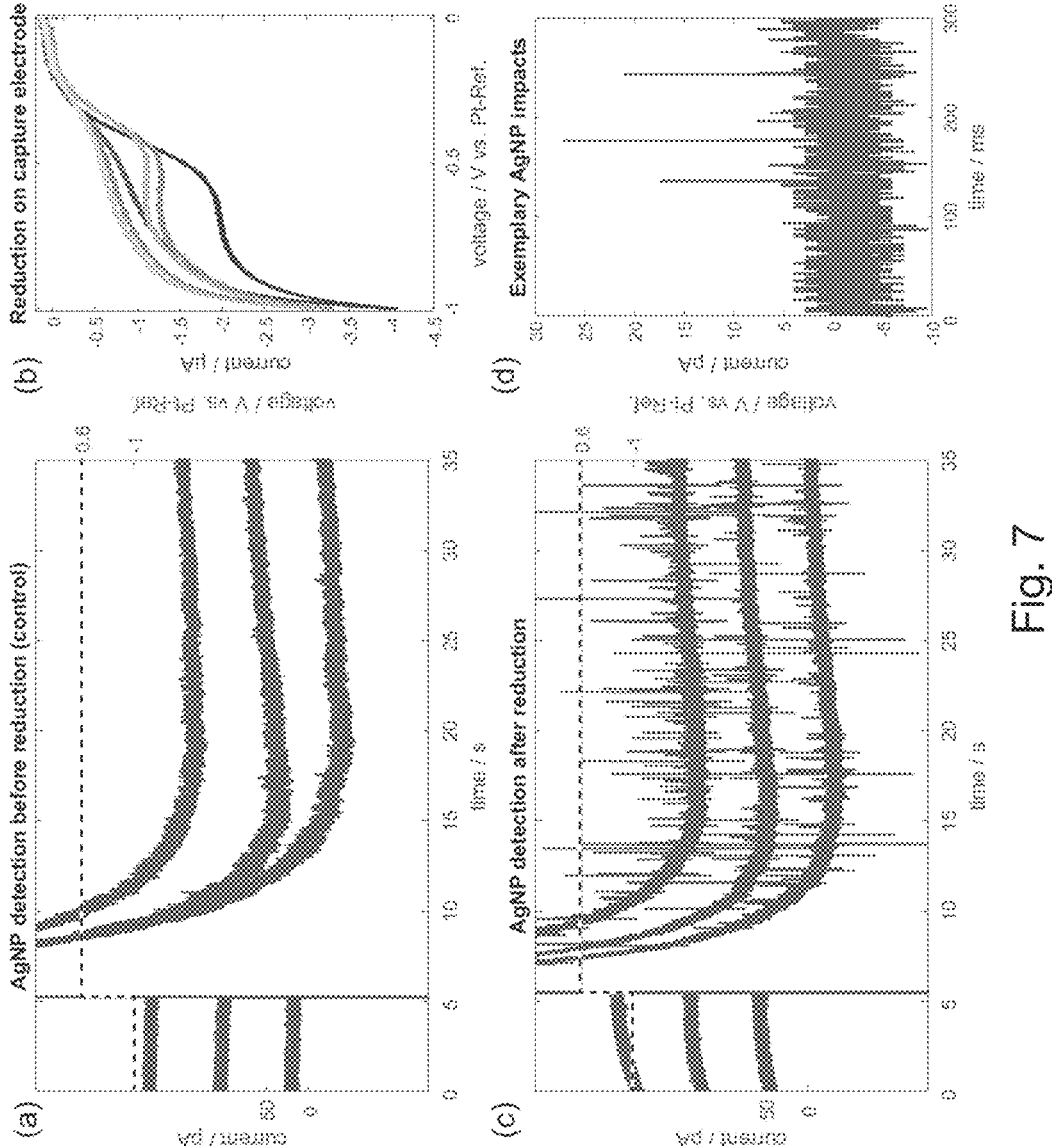

FIG. 7a depicts the experimentally measured current (solid lines) through the detection electrode of the sensor as a function of time for a control measurement in which no dissociation voltage was applied to the capture electrode. The dashed line depicts the bias voltage applied to the detection electrode relative to a platinum reference electrode, which is initially at −1.0 V and then set to +0.6 V to initiate the measurement. The three curves show three parallel recordings from three different detection microelectrodes within a single experiment. An offset is introduced for clarity of the Figure. The dissociation voltage of −1V vs platinum is applied for 30 second before applying the oxidation voltage of +0.6V to remove the residual capture monolayer on the detection electrodes, hence, to generate electroactive areas. Without applying a dissociation voltage to the capture electrode, no nanoparticles are released from the capture surface and thus no nanoparticles are present in the vicinity of the detection electrode. Accordingly, the current evolves smoothly over time and does not exhibit transient spikes in this background signal.

FIG. 7b shows the experimentally measured current through the capture electrode as a function of the applied dissociation voltage relative to a Ag/AgCl reference electrode. A prominent reduction current is observed at voltages below −0.4 V indicating the release of the nanoparticles from the capture surface by electrochemically induced dissociation. The graph shows 3 subsequent cycles of a cyclic voltammetry measurement (scan rate 100 mV/s) that reduces the thiol bonds between the capture molecules and the electrodes and furthermore strips off the silver nanoparticles. The current between −0.6 to −0.8 V is related to the reduction of the metal-thiol bond at the surface. Thus, a decreasing current amplitude for cycle 2 and 3 (grey lines) indicates that most of the metal-thiol bonds are broken in the first cycle (black line) and the silver nanoparticles are stripped off. The reduction does not have to be performed as a cyclic voltammetry recording but could be implemented with a simple voltage step. However, this representation can be compared to reference literature for the breaking of sulfur-metal bonds (Williams 2007, Cancino 2012) and shows the evolution of the release of capture molecules.

FIG. 7c depicts experimentally measured currents (solid lines) through three detection microelectrodes of the sensor array as a function of time for a measurement in which the particles on the capture electrode were dissociated using the cyclic voltage sweep shown in FIG. 7b directly before the measurement. The dashed line depicts the bias voltage applied to the detection electrode relative to the reference electrode, which is initially at −1.0 V and then set to +0.6 V to initiate the measurement. Applying the dissociation voltage at the detection electrodes ensures that the electrodes are not covered with the capture molecules, leading to free electroactive sites on the detection electrodes. The nanoparticles released from the capture surface subsequently diffuse from the capture electrode through the measurement chamber and may impact on the detection surface. During impact, a nanoparticle can undergo an electrochemical reaction, which results in a transient current spike at the detection electrode. An exemplary time trace of the current through a detection microelectrode is shown in FIG. 7d, which clearly demonstrates that individual spikes, each of which is associated with the impact of a single nanoparticle, can be identified in the measurement signal. Based on the spike rate, the concentration of the target molecules in the analyte solution may be determined, e.g. using a calibration curve that accounts for the sensor geometry, in particular the layout of the electrodes and the measurement chamber.

Furthermore, the shape and size of the current spikes can be determined, for example to identify different types of nanoparticles and thus different types of target molecules, e.g. as detailed above.

The embodiments of the present invention disclosed herein only constitute specific examples for illustration purposes. The present invention can be implemented in various ways and with many modifications without altering the underlying basic properties. Therefore, the present invention is only defined by the claims as stated below.

LIST OF REFERENCE SIGNS

100—sensor for sensing target molecules in an analyte solution
102—target molecule
104—microfluidic chamber
104A—bottom wall of the microfluidic chamber 104
106—inner volume of the microfluidic chamber
108—inlet
110—outlet
112—capture electrode
112A—capture surface
114—detection electrode
114A—detection surface
116—capture molecule
118—electrical connector
120—flow path from the capture surface 112A to the outlet 108
200—sensor for sensing target molecules in an analyte solution
114-I, 114-II—detection electrodes
202—microelectrode
210—sensor for sensing target molecules in an analyte solution
220—sensor for sensing target molecules in an analyte solution
222—support electrode
224—reference electrode
300—measurement system for sensing target molecules in an analyte solution
302—sensor
304—voltage source
306—ammeter
308—controller
400—method for sensing target molecules in an analyte solution
402—step of providing capture and detection electrodes
404—step of exposing the capture electrode to an analyte solution
406—step of exposing the capture electrode to a solution containing detection molecules
408—step of releasing nanoparticles bound to the capture electrode
410—step of determining an electrical signal
502—analyte solution
504—solution containing detection molecules
506—detection molecule
506A—electrochemically active nanoparticle
506B—functional group of detection molecule 506
508—measurement solution
510—free electrons 512—ion
600—measurement signal
600A—zoomed-in portion of the measurement signal 600
602—spike associated with target molecule of a first kind
604—spike associated with target molecule of a second kind

What is claimed is:

1. A measurement system for sensing target molecules in an analyte solution using a sensor comprising a capture surface and a detection electrode, the measurement system comprising:

an ammeter configured to measure a current through the detection electrode; and a controller for controlling the ammeter, wherein the controller is configured to:

initiate a dissociation process to release electrochemically active nanoparticles adsorbed on the capture surface;

determine a measurement signal characterizing the current through the detection electrode as a function of time using the ammeter after initiating the dissociation process; and determine a number of impact events from the measurement signal, wherein each of said impact events is a feature in the measurement signal caused by an electrochemical reaction during impact of one of said nanoparticles released from the capture surface on the detection electrode.

2. The measurement system of claim 1, wherein the controller is configured to determine the number of impact events by identifying spikes in the measurement signal.

3. The measurement system of claim 1, wherein the capture surface is a surface of an electrode and the controller is configured to:

control a voltage source that is configured to apply a voltage between the electrode comprising the capture surface and a reference electrode, wherein the reference electrode is an internal reference electrode of the sensor or an external reference electrode of the measurement system; and initiate the dissociation process by applying a dissociation voltage between the electrode comprising the capture surface and the reference electrode via the voltage source to release electrochemically active nanoparticles adsorbed on the capture surface by one or both of electrically induced dissociation and by electrochemically induced dissociation.

4. The measurement system of claim 3, wherein the capture surface is a surface of a first capture electrode and the sensor further comprises a second capture electrode, wherein the controller is configured to:

apply a dissociation voltage to the second capture electrode via the voltage source after applying the dissociation voltage to the first capture electrode and after determining the measurement signal.

5. The measurement system of claim 1, wherein the electrochemically active nanoparticles are metal nanoparticles and wherein the controller is configured to determine a size of one of the metal nanoparticles by determining one or both of an amplitude and a time-integrated current associated with an impact event of said impact events.

* * * * *